(12) United States Patent
Kornerup et al.

(10) Patent No.: US 8,287,516 B2
(45) Date of Patent: Oct. 16, 2012

(54) INFUSION SET

(75) Inventors: Grete Kornerup, Vipperød (DK); Lasse W. Mogensen, Søborg (DK); Magnus W. Göransson, Malmö (SE)

(73) Assignee: Unomedical A/S, Birkeroed (DK)

( * ) Notice: Subject to any disclaimer, the term of this patent is extended or adjusted under 35 U.S.C. 154(b) by 1678 days.

(21) Appl. No.: 10/594,048

(22) Filed: Sep. 25, 2006

(65) Prior Publication Data

US 2008/0119792 A1    May 22, 2008

Related U.S. Application Data

(63) Continuation of application No. PCT/DK2005/000189, filed on Mar. 21, 2005.

(60) Provisional application No. 60/556,863, filed on Mar. 26, 2004.

(30) Foreign Application Priority Data

Mar. 26, 2004  (DK) .................................. 2004 00493

(51) Int. Cl.
*A61M 25/16* (2006.01)
(52) U.S. Cl. ........................................ 604/533; 604/180
(58) Field of Classification Search ............... 604/93.01, 604/164.01, 180, 264, 272, 174, 533–535, 604/537–539
See application file for complete search history.

(56) References Cited

U.S. PATENT DOCUMENTS

| | | |
|---|---|---|
| 1,592,462 A | 7/1926 | MacGregor |
| 2,047,010 A | 7/1936 | Dickinson |
| 2,295,849 A | 9/1942 | Kayden |
| 2,690,529 A | 9/1954 | Lindblad |
| 2,936,141 A | 5/1960 | Rapata |
| 2,972,779 A | 2/1961 | Cowley |
| 3,059,802 A | 10/1962 | Mitchell |

(Continued)

FOREIGN PATENT DOCUMENTS

DE    4 342 329 A1    6/1994

(Continued)

OTHER PUBLICATIONS

UNOMEDICAL  A/S:  "http://web.archive.org/web/20040906102448/http://www.infusionset-set.com/Default.asp?ID=108" Internet Product Overview, Sep. 6, 2004, XP002408230.

(Continued)

*Primary Examiner* — Theodore Stigell
(74) *Attorney, Agent, or Firm* — Brinks Hofer Gilson & Lione

(57) ABSTRACT

The invention relates to an infusion set for an intermittent or continuous administration of a therapeutical substance, such as insulin. The infusion set comprises an infusion part (OB) for insertion into a patient and a connector (OA) for connecting the infusion part with a medical device through a tube (7), the connector being axially displaceable relative to the infusion part. The infusion part comprises an adhesive support (1), a base part (2) with a first set of guiding means (13) and at least two retention devices (4) for locking the connector to the infusion part, a cannula extending from said base part and being in fluid communication with a cavity which is optionally covered with a membrane, the cavity is further adapted to receive a second cannula extending from the connector, which second cannula is in fluid communication with the tube.

27 Claims, 27 Drawing Sheets

U.S. PATENT DOCUMENTS

| | | | |
|---|---|---|---|
| 3,074,541 A | 1/1963 | Roehr | |
| 3,221,739 A | 12/1965 | Rosenthal | |
| 3,221,740 A | 12/1965 | Rosenthal | |
| 3,306,291 A | 2/1967 | Burke | |
| 3,485,352 A | 12/1969 | Pilger | |
| 3,509,879 A | 5/1970 | Bathish et al. | |
| 3,519,158 A | 7/1970 | Anderson | |
| 3,545,286 A | 12/1970 | Stenstrom | |
| 3,547,119 A | 12/1970 | Hall et al. | |
| 3,610,240 A | 10/1971 | Harautuneian | |
| 3,670,727 A * | 6/1972 | Reiterman | 604/177 |
| 3,783,895 A | 1/1974 | Weichselbaum | |
| 3,788,374 A | 1/1974 | Saijo | |
| 3,810,469 A | 5/1974 | Hurschman | |
| 3,840,011 A | 10/1974 | Wright | |
| 3,893,448 A * | 7/1975 | Brantigan | 600/364 |
| 3,937,219 A | 2/1976 | Karakashian | |
| 3,986,507 A | 10/1976 | Watt | |
| 3,986,508 A | 10/1976 | Barrington | |
| 3,995,518 A | 12/1976 | Spiroff | |
| 4,022,205 A | 5/1977 | Tenczar | |
| 4,188,950 A | 2/1980 | Wardlaw | |
| 4,201,406 A | 5/1980 | Dennehey et al. | |
| 4,227,528 A | 10/1980 | Wardlaw | |
| 4,259,276 A | 3/1981 | Rawlings | |
| 4,267,836 A | 5/1981 | Whitney et al. | |
| 4,296,786 A | 10/1981 | Brignola | |
| 4,315,505 A | 2/1982 | Crandall et al. | |
| 4,333,455 A | 6/1982 | Bodicky | |
| 4,334,551 A | 6/1982 | Pfister | |
| D267,199 S | 12/1982 | Koenig | |
| 4,378,015 A | 3/1983 | Wardlaw | |
| 4,415,393 A | 11/1983 | Grimes | |
| 4,417,886 A | 11/1983 | Frankhouser et al. | |
| 4,464,178 A | 8/1984 | Dalton | |
| 4,473,369 A | 9/1984 | Lueders et al. | |
| 4,484,910 A | 11/1984 | Sarnoff et al. | |
| 4,500,312 A | 2/1985 | McFarlane | |
| 4,525,157 A | 6/1985 | Vaillancourt | |
| 4,530,695 A | 7/1985 | Phillips et al. | |
| 4,531,937 A | 7/1985 | Yates | |
| 4,563,177 A | 1/1986 | Kamen | |
| 4,610,469 A | 9/1986 | Wolff-Mooij | |
| 4,617,019 A | 10/1986 | Fecht | |
| 4,713,059 A | 12/1987 | Bickelhaupt et al. | |
| 4,734,092 A | 3/1988 | Millerd | |
| 4,755,173 A | 7/1988 | Konopka et al. | |
| 4,758,020 A | 7/1988 | Boyd | |
| 4,800,629 A | 1/1989 | Ikeda | |
| 4,817,603 A | 4/1989 | Turner et al. | |
| RE32,922 E | 5/1989 | Levin et al. | |
| 4,838,871 A | 6/1989 | Luther | |
| 4,840,613 A | 6/1989 | Balbierz | |
| 4,850,974 A | 7/1989 | Bickelhaupt et al. | |
| 4,850,996 A | 7/1989 | Cree | |
| 4,863,016 A | 9/1989 | Fong et al. | |
| 4,878,897 A | 11/1989 | Katzin | |
| 4,890,608 A | 1/1990 | Steer | |
| 4,894,054 A | 1/1990 | Miskinyar | |
| 4,895,570 A | 1/1990 | Larkin | |
| 4,917,669 A | 4/1990 | Bonaldo | |
| 4,935,010 A | 6/1990 | Cox et al. | |
| 4,950,163 A | 8/1990 | Zimble | |
| 4,950,252 A | 8/1990 | Luther et al. | |
| 4,978,338 A | 12/1990 | Melsky et al. | |
| 4,982,842 A | 1/1991 | Hollister | |
| 4,986,817 A | 1/1991 | Code | |
| 4,994,042 A | 2/1991 | Vadher | |
| 4,994,045 A | 2/1991 | Ranford | |
| 5,011,475 A | 4/1991 | Olson | |
| 5,020,665 A | 6/1991 | Bruno | |
| 5,024,662 A | 6/1991 | Menes et al. | |
| 5,067,496 A | 11/1991 | Eisele | |
| 5,092,853 A | 3/1992 | Couvertier, II | |
| 5,098,389 A | 3/1992 | Cappucci | |
| 5,112,313 A | 5/1992 | Sallee | |
| 5,116,319 A | 5/1992 | Van den Haak | |
| 5,116,325 A | 5/1992 | Paterson | |
| 5,121,751 A | 6/1992 | Panalletta | |
| 5,129,884 A | 7/1992 | Dysarz | |
| 5,135,502 A | 8/1992 | Koenig, Jr. et al. | |
| 5,137,516 A | 8/1992 | Rand et al. | |
| 5,137,524 A | 8/1992 | Lynn et al. | |
| 5,141,496 A | 8/1992 | Dalto et al. | |
| 5,147,375 A | 9/1992 | Sullivan et al. | |
| 5,163,915 A | 11/1992 | Holleron | |
| 5,172,808 A | 12/1992 | Bruno | |
| 5,176,643 A | 1/1993 | Kramer et al. | |
| 5,176,650 A | 1/1993 | Haining | |
| 5,176,662 A | 1/1993 | Bartholomew et al. | |
| 5,186,712 A | 2/1993 | Kelso et al. | |
| 5,188,611 A | 2/1993 | Orgain | |
| RE34,223 E | 4/1993 | Bonaldo | |
| 5,205,820 A | 4/1993 | Kriesel | |
| 5,222,947 A | 6/1993 | D'Amico | |
| 5,232,454 A | 8/1993 | Hollister | |
| 5,248,301 A | 9/1993 | Koenig et al. | |
| 5,256,149 A | 10/1993 | Banik et al. | |
| 5,256,152 A | 10/1993 | Marks | |
| 5,257,980 A | 11/1993 | Van Antwerp et al. | |
| 5,267,963 A | 12/1993 | Bachynsky | |
| 5,269,799 A | 12/1993 | Daniel | |
| 5,271,744 A | 12/1993 | Kramer et al. | |
| 5,279,579 A | 1/1994 | D'Amico | |
| 5,279,591 A | 1/1994 | Simon | |
| 5,282,793 A | 2/1994 | Larson | |
| 5,300,030 A | 4/1994 | Crossman et al. | |
| 5,312,359 A | 5/1994 | Wallace | |
| 5,312,369 A | 5/1994 | Arcusin et al. | |
| 5,316,246 A | 5/1994 | Scott et al. | |
| 5,324,302 A | 6/1994 | Crouse | |
| 5,342,319 A | 8/1994 | Watson et al. | |
| 5,342,324 A | 8/1994 | Tucker | |
| 5,350,392 A | 9/1994 | Purcell et al. | |
| 5,354,280 A | 10/1994 | Haber et al. | |
| 5,366,469 A | 11/1994 | Steg et al. | |
| 5,372,592 A | 12/1994 | Gambale | |
| 5,372,787 A | 12/1994 | Ritter | |
| 5,376,082 A | 12/1994 | Phelps | |
| 5,379,895 A | 1/1995 | Foslien | |
| 5,380,067 A | 1/1995 | Turvill et al. | |
| 5,384,174 A | 1/1995 | Ward et al. | |
| 5,387,197 A | 2/1995 | Smith et al. | |
| 5,388,931 A | 2/1995 | Carlson | |
| 5,390,669 A | 2/1995 | Stuart et al. | |
| 5,391,151 A | 2/1995 | Wilmot | |
| 5,403,288 A | 4/1995 | Stanners | |
| 5,405,332 A | 4/1995 | Opalek | |
| 5,429,607 A | 7/1995 | McPhee | |
| 5,429,613 A | 7/1995 | D'Amico | |
| 5,433,307 A | 7/1995 | Jeppe | |
| 5,439,473 A | 8/1995 | Jorgensen | |
| D362,718 S | 9/1995 | Deily et al. | |
| 5,449,349 A | 9/1995 | Sallee et al. | |
| 5,451,210 A | 9/1995 | Kramer et al. | |
| 5,487,506 A | 1/1996 | Drummond et al. | |
| 5,490,841 A | 2/1996 | Landis | |
| 5,492,313 A | 2/1996 | Pan et al. | |
| 5,501,675 A | 3/1996 | Erskine | |
| 5,505,709 A | 4/1996 | Funderburk et al. | |
| 5,507,730 A | 4/1996 | Haber et al. | |
| 5,514,117 A | 5/1996 | Lynn | |
| 5,519,167 A | 5/1996 | Kunimoto et al. | |
| 5,520,654 A | 5/1996 | Wahlberg | |
| 5,522,803 A | 6/1996 | Teissen-Simony | |
| 5,527,287 A | 6/1996 | Miskinyar et al. | |
| 5,533,974 A | 7/1996 | Gaba | |
| 5,540,709 A | 7/1996 | Ramel | |
| 5,545,143 A | 8/1996 | Fischell | |
| 5,545,152 A | 8/1996 | Funderburk et al. | |
| 5,549,577 A | 8/1996 | Siegel et al. | |
| 5,554,130 A | 9/1996 | McDonald et al. | |
| 5,558,650 A | 9/1996 | McPhee | |
| 5,562,629 A | 10/1996 | Haughton et al. | |
| 5,562,636 A | 10/1996 | Utterberg | |
| 5,573,510 A | 11/1996 | Isaacson | |
| 5,575,777 A | 11/1996 | Cover et al. | |

| | | | | | | |
|---|---|---|---|---|---|---|
| 5,584,813 A | 12/1996 | Livingston et al. | 6,086,575 A | 7/2000 | Mejslov | |
| 5,586,553 A | 12/1996 | Halili | 6,090,068 A | 7/2000 | Chanut | |
| 5,591,188 A | 1/1997 | Waisman | 6,093,172 A | 7/2000 | Funderburk et al. | |
| 5,599,309 A | 2/1997 | Marshall et al. | 6,093,179 A | 7/2000 | O'Hara et al. | |
| 5,599,315 A | 2/1997 | McPhee | 6,099,503 A | 8/2000 | Stradella | |
| 5,599,318 A | 2/1997 | Sweeney et al. | 6,105,218 A | 8/2000 | Reekie | |
| 5,628,765 A | 5/1997 | Morita | 6,106,498 A | 8/2000 | Friedli et al. | |
| 5,643,214 A | 7/1997 | Marshall | 6,120,482 A | 9/2000 | Szabo | |
| 5,643,216 A | 7/1997 | White | 6,123,690 A * | 9/2000 | Mejslov | 604/533 |
| 5,643,220 A | 7/1997 | Cosme | 6,132,755 A | 10/2000 | Eicher et al. | |
| 5,662,617 A | 9/1997 | Odell et al. | 6,139,534 A | 10/2000 | Niedospial, Jr. | |
| 5,665,071 A | 9/1997 | Wyrick | 6,159,181 A | 12/2000 | Crossman et al. | |
| 5,665,075 A | 9/1997 | Gyure et al. | 6,183,464 B1 | 2/2001 | Sharp et al. | |
| 5,676,156 A | 10/1997 | Yoon | 6,191,338 B1 | 2/2001 | Haller | |
| 5,681,323 A | 10/1997 | Arick | 6,193,694 B1 | 2/2001 | Bell et al. | |
| 5,695,476 A | 12/1997 | Harris | 6,210,420 B1 | 4/2001 | Mauze et al. | |
| 5,697,907 A * | 12/1997 | Gaba .......................... 604/110 | 6,219,574 B1 | 4/2001 | Cormier et al. | |
| 5,700,250 A | 12/1997 | Erskine | 6,221,058 B1 | 4/2001 | Kao et al. | |
| 5,702,371 A | 12/1997 | Bierman | 6,248,093 B1 | 6/2001 | Moberg | |
| 5,704,920 A | 1/1998 | Gyure | 6,293,925 B1 | 9/2001 | Safabash et al. | |
| 5,709,516 A | 1/1998 | Peterson et al. | 6,302,866 B1 | 10/2001 | Marggi | |
| 5,714,225 A | 2/1998 | Hansen et al. | 6,319,232 B1 | 11/2001 | Kashmer | |
| 5,738,641 A | 4/1998 | Watson et al. | 6,322,535 B1 | 11/2001 | Hitchins et al. | |
| 5,741,288 A | 4/1998 | Rife | 6,322,808 B1 | 11/2001 | Trautman et al. | |
| 5,752,923 A | 5/1998 | Terwilliger | 6,334,856 B1 | 1/2002 | Allen et al. | |
| 5,807,316 A | 9/1998 | Teeple | 6,355,021 B1 | 3/2002 | Nielsen et al. | |
| 5,807,348 A | 9/1998 | Zinger et al. | 6,379,335 B1 | 4/2002 | Rigon et al. | |
| 5,810,835 A | 9/1998 | Ryan et al. | D456,692 S | 5/2002 | Epstein | |
| 5,817,058 A | 10/1998 | Shaw | 6,387,076 B1 | 5/2002 | Van Landuyt | |
| 5,820,598 A | 10/1998 | Gazza et al. | 6,387,078 B1 | 5/2002 | Gillespie, III | |
| 5,827,236 A | 10/1998 | Takahashi | 6,405,876 B1 | 6/2002 | Seshimoto et al. | |
| 5,833,666 A | 11/1998 | Davis et al. | 6,440,096 B1 | 8/2002 | Lastovich et al. | |
| D402,538 S | 12/1998 | Wagter et al. | 6,447,482 B1 | 9/2002 | Rønborg et al. | |
| 5,843,001 A | 12/1998 | Goldenberg | 6,450,992 B1 | 9/2002 | Cassidy, Jr. | |
| 5,848,990 A | 12/1998 | Cirelli et al. | 6,485,461 B1 | 11/2002 | Mason et al. | |
| 5,851,197 A | 12/1998 | Marano et al. | 6,488,663 B1 | 12/2002 | Steg | |
| 5,858,001 A | 1/1999 | Tsals et al. | 6,503,222 B2 | 1/2003 | Lo | |
| 5,865,806 A | 2/1999 | Howell | 6,517,517 B1 | 2/2003 | Farrugia et al. | |
| 5,873,540 A | 2/1999 | Hardin | 6,520,938 B1 | 2/2003 | Funderburk et al. | |
| 5,899,886 A | 5/1999 | Cosme | D472,316 S | 3/2003 | Douglas et al. | |
| 5,911,705 A | 6/1999 | Howell | D472,630 S | 4/2003 | Douglas et al. | |
| 5,913,846 A | 6/1999 | Szabo | 6,572,586 B1 | 6/2003 | Wojcik | |
| 5,915,640 A | 6/1999 | Wagter et al. | 6,579,267 B2 | 6/2003 | Lynch et al. | |
| 5,916,199 A | 6/1999 | Miles | 6,582,397 B2 | 6/2003 | Alesi et al. | |
| 5,919,167 A | 7/1999 | Mulhauser et al. | 6,595,962 B1 | 7/2003 | Perthu | |
| 5,919,170 A | 7/1999 | Woessner | 6,607,509 B2 | 8/2003 | Bobroff et al. | |
| 5,925,032 A | 7/1999 | Clements | 6,607,511 B2 | 8/2003 | Halseth et al. | |
| 5,935,109 A | 8/1999 | Donnan | 6,613,064 B2 | 9/2003 | Rutynowski et al. | |
| 5,947,931 A | 9/1999 | Bierman | 6,620,133 B1 | 9/2003 | Steck | |
| 5,947,935 A | 9/1999 | Rhinehart et al. | 6,620,136 B1 | 9/2003 | Pressly, Sr. et al. | |
| 5,951,523 A | 9/1999 | Osterlind et al. | 6,620,140 B1 | 9/2003 | Metzger | |
| 5,954,643 A | 9/1999 | VanAntwerp et al. | 6,629,949 B1 | 10/2003 | Douglas | |
| 5,957,892 A | 9/1999 | Thorne | 6,645,181 B1 | 11/2003 | Lavi et al. | |
| 5,968,011 A | 10/1999 | Larsen et al. | 6,645,182 B1 | 11/2003 | Szabo | |
| 5,975,120 A | 11/1999 | Novosel | 6,659,982 B2 | 12/2003 | Douglas et al. | |
| 5,980,488 A | 11/1999 | Thorne | 6,685,674 B2 | 2/2004 | Douglas et al. | |
| 5,980,506 A | 11/1999 | Mathiasen | 6,699,218 B2 | 3/2004 | Flaherty et al. | |
| 5,984,224 A | 11/1999 | Yang | 6,702,779 B2 | 3/2004 | Connelly et al. | |
| 5,984,897 A | 11/1999 | Petersen et al. | 6,726,649 B2 | 4/2004 | Swenson et al. | |
| 5,992,787 A | 11/1999 | Burke | 6,736,797 B1 | 5/2004 | Larsen et al. | |
| D417,733 S | 12/1999 | Howell et al. | 6,749,587 B2 | 6/2004 | Flaherty | |
| 6,017,328 A | 1/2000 | Fischell et al. | 6,749,589 B1 | 6/2004 | Douglas et al. | |
| 6,017,598 A | 1/2000 | Kreischer et al. | 6,755,805 B1 | 6/2004 | Reid | |
| D421,119 S | 2/2000 | Musgrave et al. | 6,776,775 B1 | 8/2004 | Mohammad | |
| 6,024,727 A | 2/2000 | Thorne et al. | 6,790,199 B1 | 9/2004 | Gianakos | |
| 6,039,629 A | 3/2000 | Mitchell | 6,805,686 B1 | 10/2004 | Fathallah et al. | |
| 6,042,570 A | 3/2000 | Bell et al. | 6,808,506 B2 | 10/2004 | Lastovich et al. | |
| 6,045,533 A | 4/2000 | Kriesel et al. | 6,811,545 B2 | 11/2004 | Vaillancourt | |
| 6,045,534 A | 4/2000 | Jacobsen et al. | 6,814,720 B2 | 11/2004 | Olsen et al. | |
| 6,050,976 A | 4/2000 | Thorne et al. | 6,824,530 B2 | 11/2004 | Wagner et al. | |
| 6,053,893 A | 4/2000 | Bucher | 6,824,531 B1 | 11/2004 | Zecha, Jr. et al. | |
| 6,053,930 A | 4/2000 | Ruppert | 6,830,562 B2 | 12/2004 | Mogensen et al. | |
| 6,056,718 A | 5/2000 | Funderburk et al. | 6,837,877 B2 | 1/2005 | Zurcher | |
| 6,056,726 A | 5/2000 | Isaacson | 6,837,878 B2 | 1/2005 | Smutney et al. | |
| 6,074,369 A | 6/2000 | Sage et al. | 6,840,922 B2 | 1/2005 | Nielsen et al. | |
| 6,074,371 A | 6/2000 | Fischell | 6,880,701 B2 | 4/2005 | Bergeron et al. | |
| 6,077,244 A | 6/2000 | Botich et al. | 6,916,017 B2 | 7/2005 | Noe | |
| 6,079,432 A | 6/2000 | Paradis | 6,923,791 B2 | 8/2005 | Douglas | |
| 6,086,008 A | 7/2000 | Gray et al. | 6,926,694 B2 | 8/2005 | Marano-Ford et al. | |

| | | |
|---|---|---|
| 6,939,331 B2 | 9/2005 | Ohshima |
| 6,949,084 B2 | 9/2005 | Marggi et al. |
| 6,959,812 B2 | 11/2005 | Reif et al. |
| 6,960,193 B2 | 11/2005 | Rosenberg |
| 6,979,316 B1 | 12/2005 | Rubin et al. |
| 6,991,619 B2 | 1/2006 | Marano-Ford et al. |
| 6,991,620 B2 | 1/2006 | Marano-Ford et al. |
| 6,994,213 B2 | 2/2006 | Giard et al. |
| 6,997,907 B2 | 2/2006 | Safabash et al. |
| 7,014,625 B2 | 3/2006 | Bengtsson |
| 7,018,344 B2 | 3/2006 | Bressler et al. |
| 7,022,108 B2 | 4/2006 | Marano-Ford et al. |
| 7,047,070 B2 | 5/2006 | Wilkenson et al. |
| 7,052,483 B2 | 5/2006 | Wojcik |
| 7,055,713 B2 | 6/2006 | Rea et al. |
| 7,056,302 B2 | 6/2006 | Douglas |
| 7,070,580 B2 | 7/2006 | Nielsen |
| 7,074,208 B2 | 7/2006 | Pajunk et al. |
| D526,409 S | 8/2006 | Nielsen et al. |
| 7,083,592 B2 | 8/2006 | Lastovich et al. |
| 7,083,597 B2 | 8/2006 | Lynch et al. |
| 7,097,631 B2 | 8/2006 | Trautman et al. |
| 7,109,878 B2 | 9/2006 | Mann et al. |
| 7,115,108 B2 | 10/2006 | Wilkenson et al. |
| 7,115,112 B2 | 10/2006 | Mogensen et al. |
| 7,141,023 B2 | 11/2006 | Diermann et al. |
| 7,147,623 B2 | 12/2006 | Mathiasen |
| 7,186,236 B2 | 3/2007 | Gibson et al. |
| 7,211,068 B2 | 5/2007 | Douglas |
| 7,214,207 B2 | 5/2007 | Lynch et al. |
| 7,214,215 B2 | 5/2007 | Heinzerling et al. |
| 7,250,037 B2 | 7/2007 | Shermer et al. |
| 7,258,680 B2 | 8/2007 | Mogensen et al. |
| D554,253 S | 10/2007 | Kornerup |
| 7,303,543 B1 | 12/2007 | Maule et al. |
| 7,309,326 B2 | 12/2007 | Fangrow, Jr. |
| 7,407,491 B2 | 8/2008 | Fangrow, Jr. |
| 7,407,493 B2 | 8/2008 | Cane' |
| 7,431,876 B2 | 10/2008 | Mejlhede et al. |
| 7,441,655 B1 | 10/2008 | Hoftman |
| 7,520,867 B2 * | 4/2009 | Bowman et al. ............ 604/93.01 |
| 7,569,262 B2 | 8/2009 | Szabo et al. |
| 7,648,494 B2 | 1/2010 | Kornerup et al. |
| 7,766,867 B2 | 8/2010 | Lynch et al. |
| 2001/0004970 A1 | 6/2001 | Hollister et al. |
| 2001/0016714 A1 | 8/2001 | Bell et al. |
| 2001/0021827 A1 | 9/2001 | Ferguson et al. |
| 2001/0039387 A1 | 11/2001 | Rutynowski et al. |
| 2001/0039401 A1 | 11/2001 | Ferguson et al. |
| 2001/0041875 A1 | 11/2001 | Higuchi et al. |
| 2001/0049496 A1 | 12/2001 | Kirchhofer |
| 2001/0053889 A1 * | 12/2001 | Marggi et al. ............ 604/164.11 |
| 2001/0056284 A1 | 12/2001 | Purcell et al. |
| 2002/0022798 A1 | 2/2002 | Connelly |
| 2002/0022855 A1 | 2/2002 | Bobroff et al. |
| 2002/0026152 A1 | 2/2002 | Bierman |
| 2002/0055711 A1 | 5/2002 | Lavi et al. |
| 2002/0068904 A1 | 6/2002 | Pluth et al. |
| 2002/0072720 A1 | 6/2002 | Hague et al. |
| 2002/0074345 A1 | 6/2002 | Schneider et al. |
| 2002/0077599 A1 | 6/2002 | Wojcik |
| 2002/0082543 A1 | 6/2002 | Park et al. |
| 2002/0107489 A1 | 8/2002 | Lee |
| 2002/0111581 A1 | 8/2002 | Sasso |
| 2002/0145073 A1 | 10/2002 | Swanson et al. |
| 2002/0156424 A1 | 10/2002 | Suzuki et al. |
| 2002/0156427 A1 | 10/2002 | Suzuki et al. |
| 2002/0161322 A1 | 10/2002 | Utterberg et al. |
| 2002/0161332 A1 | 10/2002 | Ramey |
| 2002/0161386 A1 | 10/2002 | Halseth et al. |
| 2002/0165493 A1 | 11/2002 | Bierman |
| 2002/0169419 A1 | 11/2002 | Steg |
| 2002/0173748 A1 | 11/2002 | McConnell et al. |
| 2002/0173769 A1 | 11/2002 | Gray et al. |
| 2002/0183688 A1 | 12/2002 | Lastovich et al. |
| 2002/0189688 A1 | 12/2002 | Roorda |
| 2002/0193737 A1 | 12/2002 | Popovsky |
| 2002/0193744 A1 | 12/2002 | Alesi et al. |
| 2003/0014018 A1 | 1/2003 | Giambattista et al. |
| 2003/0060781 A1 | 3/2003 | Mogensen et al. |
| 2003/0069548 A1 | 4/2003 | Connelly et al. |
| 2003/0088238 A1 | 5/2003 | Poulsen et al. |
| 2003/0105430 A1 | 6/2003 | Lavi et al. |
| 2003/0109829 A1 | 6/2003 | Mogensen et al. |
| 2003/0125669 A1 | 7/2003 | Safabash et al. |
| 2003/0125678 A1 | 7/2003 | Swenson et al. |
| 2003/0130619 A1 | 7/2003 | Safabash et al. |
| 2003/0139704 A1 | 7/2003 | Lin |
| 2003/0158520 A1 | 8/2003 | Safabash et al. |
| 2003/0176843 A1 | 9/2003 | Wilkinson |
| 2003/0176852 A1 | 9/2003 | Lynch et al. |
| 2003/0181863 A1 | 9/2003 | Ackley et al. |
| 2003/0181868 A1 | 9/2003 | Swenson |
| 2003/0181873 A1 | 9/2003 | Swenson |
| 2003/0181874 A1 | 9/2003 | Bressler et al. |
| 2003/0187394 A1 | 10/2003 | Wilkinson et al. |
| 2003/0187395 A1 | 10/2003 | Wilkinson et al. |
| 2003/0199823 A1 | 10/2003 | Bobroff et al. |
| 2003/0216686 A1 | 11/2003 | Lynch et al. |
| 2003/0220610 A1 | 11/2003 | Lastovich et al. |
| 2003/0225373 A1 | 12/2003 | Bobroff et al. |
| 2003/0225374 A1 | 12/2003 | Mathiasen |
| 2003/0229308 A1 | 12/2003 | Tsals et al. |
| 2003/0229316 A1 | 12/2003 | Hwang et al. |
| 2004/0002682 A1 | 1/2004 | Kovelman et al. |
| 2004/0006316 A1 | 1/2004 | Patton |
| 2004/0026840 A1 | 2/2004 | Eckel et al. |
| 2004/0044306 A1 | 3/2004 | Lynch et al. |
| 2004/0049159 A1 | 3/2004 | Barrus et al. |
| 2004/0059316 A1 | 3/2004 | Smedegaard |
| 2004/0068231 A1 | 4/2004 | Blondeau |
| 2004/0069044 A1 | 4/2004 | Lavi et al. |
| 2004/0087913 A1 | 5/2004 | Rogers et al. |
| 2004/0092875 A1 | 5/2004 | Kochamba |
| 2004/0111068 A1 | 6/2004 | Swenson |
| 2004/0112781 A1 | 6/2004 | Hofverberg et al. |
| 2004/0116865 A1 | 6/2004 | Bengtsson |
| 2004/0133164 A1 | 7/2004 | Funderburk et al. |
| 2004/0138612 A1 | 7/2004 | Shermer et al. |
| 2004/0138620 A1 | 7/2004 | Douglas et al. |
| 2004/0143216 A1 | 7/2004 | Douglas et al. |
| 2004/0143218 A1 | 7/2004 | Das |
| 2004/0158202 A1 | 8/2004 | Jensen |
| 2004/0158207 A1 | 8/2004 | Hunn et al. |
| 2004/0162518 A1 | 8/2004 | Connelly et al. |
| 2004/0171989 A1 | 9/2004 | Horner et al. |
| 2004/0178098 A1 | 9/2004 | Swenson et al. |
| 2004/0186446 A1 | 9/2004 | Ohshima |
| 2004/0193143 A1 | 9/2004 | Sauer |
| 2004/0199123 A1 | 10/2004 | Nielsen |
| 2004/0204673 A1 | 10/2004 | Flaherty et al. |
| 2004/0204687 A1 | 10/2004 | Mogensen et al. |
| 2004/0204690 A1 | 10/2004 | Yashiro et al. |
| 2004/0215151 A1 | 10/2004 | Marshall et al. |
| 2004/0220528 A1 | 11/2004 | Garcia, Jr. |
| 2004/0236284 A1 | 11/2004 | Hoste et al. |
| 2004/0238392 A1 | 12/2004 | Peterson et al. |
| 2004/0243065 A1 | 12/2004 | McConnell et al. |
| 2004/0254433 A1 | 12/2004 | Bandis et al. |
| 2004/0260235 A1 | 12/2004 | Douglas |
| 2004/0260250 A1 | 12/2004 | Harris et al. |
| 2005/0035014 A1 | 2/2005 | Cane |
| 2005/0038378 A1 | 2/2005 | Lastovich et al. |
| 2005/0043687 A1 | 2/2005 | Mogensen et al. |
| 2005/0049571 A1 | 3/2005 | Lastovich et al. |
| 2005/0065466 A1 | 3/2005 | Vedrine |
| 2005/0065472 A1 | 3/2005 | Cindrich et al. |
| 2005/0075606 A1 | 4/2005 | Botich et al. |
| 2005/0080386 A1 | 4/2005 | Reid |
| 2005/0101910 A1 | 5/2005 | Bowman et al. |
| 2005/0101912 A1 | 5/2005 | Faust et al. |
| 2005/0101932 A1 | 5/2005 | Cote et al. |
| 2005/0101933 A1 | 5/2005 | Marrs et al. |
| 2005/0107743 A1 | 5/2005 | Fangrow, Jr. |
| 2005/0113761 A1 | 5/2005 | Faust et al. |
| 2005/0119611 A1 | 6/2005 | Marano-Ford et al. |
| 2005/0119619 A1 | 6/2005 | Haining |
| 2005/0119637 A1 | 6/2005 | Lundgren et al. |

| | | | | | | |
|---|---|---|---|---|---|---|
| 2005/0124936 | A1 | 6/2005 | Mogensen et al. | EP | 0 544 837 B1 | 6/1993 |
| 2005/0131347 | A1 | 6/2005 | Marano-Ford et al. | EP | 0 651 662 B1 | 5/1995 |
| 2005/0159709 | A1 | 7/2005 | Wilkinson | EP | 0652027 A1 | 5/1995 |
| 2005/0159714 | A1 | 7/2005 | Gibson | EP | 0 657 184 A1 | 6/1995 |
| 2005/0165382 | A1 | 7/2005 | Fulford | EP | 0 714 631 B1 | 6/1996 |
| 2005/0192560 | A1 | 9/2005 | Walls et al. | EP | 0 744 183 A2 | 11/1996 |
| 2005/0203461 | A1 | 9/2005 | Flaherty et al. | EP | 0 747 006 A1 | 12/1996 |
| 2005/0215979 | A1 | 9/2005 | Kornerup et al. | EP | 0799626 A1 | 10/1997 |
| 2005/0240154 | A1 | 10/2005 | Mogensen et al. | EP | 0 688 232 B1 | 12/1998 |
| 2005/0251098 | A1 | 11/2005 | Wyss et al. | EP | 0937475 A2 | 8/1999 |
| 2005/0256456 | A1 | 11/2005 | Marano-Ford et al. | EP | 0 956 879 A1 | 11/1999 |
| 2005/0261629 | A1 | 11/2005 | Marano-Ford et al. | EP | 0 615 768 A2 | 12/1999 |
| 2005/0277892 | A1 | 12/2005 | Chen | EP | 1 086 718 A1 | 3/2001 |
| 2005/0283114 | A1 | 12/2005 | Bresina et al. | EP | 1 125 593 A1 | 8/2001 |
| 2006/0015063 | A1 | 1/2006 | Butikofer et al. | EP | 0 775 501 B1 | 6/2002 |
| 2006/0015076 | A1 | 1/2006 | Heinzerling et al. | EP | 1 329 233 A1 | 7/2003 |
| 2006/0030815 | A1 | 2/2006 | Csincsura et al. | EP | 1350537 A1 | 10/2003 |
| 2006/0036214 | A1 | 2/2006 | Mogensen et al. | EP | 1 380 315 A1 | 1/2004 |
| 2006/0041224 | A1 | 2/2006 | Jensen | EP | 1 407 747 A1 | 4/2004 |
| 2006/0069351 | A9 | 3/2006 | Safabash et al. | EP | 1407793 A1 | 4/2004 |
| 2006/0069382 | A1 | 3/2006 | Pedersen | EP | 1 421 968 A2 | 5/2004 |
| 2006/0069383 | A1 | 3/2006 | Bogaerts et al. | EP | 1495775 A1 | 1/2005 |
| 2006/0095003 | A1 | 5/2006 | Marano-Ford et al. | EP | 1502613 A | 2/2005 |
| 2006/0095014 | A1 | 5/2006 | Ethelfeld | EP | 1525873 A1 | 4/2005 |
| 2006/0106346 | A1 | 5/2006 | Sullivan et al. | EP | 1527792 A1 | 5/2005 |
| 2006/0129123 | A1 | 6/2006 | Wojcik | EP | 1616594 A1 | 1/2006 |
| 2006/0135908 | A1 | 6/2006 | Liniger et al. | EP | 1704889 A1 | 9/2006 |
| 2006/0135913 | A1 | 6/2006 | Ethelfeld | EP | 1719537 A2 | 11/2006 |
| 2006/0142698 | A1 | 6/2006 | Ethelfeld | EP | 1762259 A1 | 3/2007 |
| 2006/0161108 | A1 | 7/2006 | Mogensen et al. | EP | 1764125 A1 | 3/2007 |
| 2006/0173410 | A1 | 8/2006 | Moberg et al. | FK | 1177802 B1 | 9/2004 |
| 2006/0173413 | A1 | 8/2006 | Fan | FR | 2725902 A1 | 10/1994 |
| 2006/0184104 | A1 | 8/2006 | Cheney, II et al. | FR | 2 752 164 A1 | 2/1998 |
| 2006/0184140 | A1 | 8/2006 | Okiyama | GB | 478803 | 1/1938 |
| 2006/0200073 | A1 | 9/2006 | Radmer et al. | GB | 906574 | 9/1962 |
| 2006/0241551 | A1 | 10/2006 | Lynch et al. | GB | 2 088 215 A | 6/1982 |
| 2006/0247553 | A1 | 11/2006 | Diermann et al. | GB | 2 230 702 A | 10/1990 |
| 2006/0247574 | A1 | 11/2006 | Maule et al. | GB | 2 423 267 A | 8/2006 |
| 2006/0253085 | A1 | 11/2006 | Geismar et al. | JP | A-03-191965 A | 8/1991 |
| 2006/0253086 | A1 | 11/2006 | Moberg et al. | JP | 7051251 A | 11/1995 |
| 2006/0264835 | A1 | 11/2006 | Nielsen et al. | JP | A-08-187286 A | 7/1996 |
| 2006/0264890 | A1 | 11/2006 | Moberg et al. | JP | A-10-179734 A | 7/1998 |
| 2007/0005017 | A1 | 1/2007 | Alchas et al. | JP | 2002-028246 A | 1/2002 |
| 2007/0016129 | A1 | 1/2007 | Liniger et al. | WO | WO 81/01795 A1 | 7/1981 |
| 2007/0016159 | A1 | 1/2007 | Sparholt et al. | WO | WO 82/03558 A1 | 10/1982 |
| 2007/0021729 | A1 | 1/2007 | Mogensen et al. | WO | WO 92/04062 A1 | 3/1992 |
| 2007/0049865 | A1 | 3/2007 | Radmer et al. | WO | WO 93/05840 A2 | 4/1993 |
| 2007/0049870 | A1 | 3/2007 | Gray et al. | WO | WO 93/11709 A1 | 6/1993 |
| 2007/0066955 | A1 | 3/2007 | Sparholt et al. | WO | WO 94/20160 A1 | 9/1994 |
| 2007/0088271 | A1 | 4/2007 | Richards et al. | WO | WO 96/20021 A1 | 7/1996 |
| 2007/0093754 | A1 | 4/2007 | Mogensen | WO | WO 96/032981 A1 | 10/1996 |
| 2007/0104596 | A1 | 5/2007 | Preuthun et al. | WO | WO 98/26835 A1 | 6/1998 |
| 2007/0112301 | A1 | 5/2007 | Preuthun et al. | WO | WO 98/33549 A1 | 8/1998 |
| 2007/0112303 | A1 | 5/2007 | Liniger | WO | WO 98/58693 A1 | 12/1998 |
| 2007/0129688 | A1 | 6/2007 | Scheurer et al. | WO | WO 99/07435 A1 | 2/1999 |
| 2007/0173767 | A1 | 7/2007 | Lynch et al. | WO | WO 99/33504 A1 | 7/1999 |
| 2007/0179444 | A1 | 8/2007 | Causey et al. | WO | WO 00/02614 A1 | 1/2000 |
| 2007/0185441 | A1 | 8/2007 | Fangrow, Jr. | WO | WO 00/03757 A1 | 1/2000 |
| 2007/0191772 | A1 | 8/2007 | Wojcik | WO | WO 00/44324 A1 | 8/2000 |
| 2007/0191773 | A1 | 8/2007 | Wojcik | WO | WO 01/30419 A2 | 5/2001 |
| 2007/0203454 | A1 | 8/2007 | Shermer et al. | WO | WO 01/68180 A1 | 9/2001 |
| 2007/0213673 | A1 | 9/2007 | Douglas | WO | WO 01/72353 A2 | 10/2001 |
| 2007/0244448 | A1 | 10/2007 | Lastovich et al. | WO | WO 01/76684 A1 | 10/2001 |
| 2008/0312601 | A1 | 12/2008 | Cane | WO | WO 01/93926 A2 | 12/2001 |
| 2010/0004597 | A1 | 1/2010 | Gyrn et al. | WO | WO 02/02165 A2 | 1/2002 |
| 2010/0137829 | A1 | 6/2010 | Nielsen et al. | WO | WO 02/07804 A1 | 1/2002 |
| 2010/0228226 | A1 | 9/2010 | Nielsen | WO | WO 02/40083 A2 | 5/2002 |
| | | | | WO | WO 02/053220 A2 | 7/2002 |
| | | FOREIGN PATENT DOCUMENTS | | WO | WO 02/081012 A2 | 10/2002 |
| DE | | 196 31 921 A1 | 3/1997 | WO | WO 02/081013 A2 | 10/2002 |
| DE | | 299 05 072 U1 | 9/1999 | WO | WO 02/083206 A2 | 10/2002 |
| DE | | 101 17 285 A1 | 11/2002 | WO | WO 02/094352 A2 | 11/2002 |
| DE | | 203 20 207 U1 | 11/2004 | WO | WO 02/100457 A2 | 12/2002 |
| DK | | EP 1 360 970 A1 | 11/2003 | WO | WO 02/102442 A1 | 12/2002 |
| DK | | EP 1 475 113 A1 | 11/2004 | WO | WO 02/068014 A3 | 1/2003 |
| EP | | 0 117 632 B1 | 9/1984 | WO | WO 03/015860 A1 | 2/2003 |
| EP | | 0 239 244 B1 | 2/1987 | WO | WO 03/026728 A1 | 4/2003 |
| EP | | 0272530 A2 | 6/1988 | WO | WO 03/068305 A1 | 8/2003 |
| EP | | 0 451 040 A1 | 10/1991 | WO | WO 03/075980 A2 | 9/2003 |

| | | | |
|---|---|---|---|
| WO | WO 03/095003 A1 | 11/2003 |
| WO | WO 2004/012796 A1 | 2/2004 |
| WO | WO 2004/029457 A1 | 4/2004 |
| WO | WO 2004/030726 A1 | 4/2004 |
| WO | WO 2004/037325 A1 | 5/2004 |
| WO | WO 2004/054644 A1 | 7/2004 |
| WO | WO 2004/056412 A2 | 7/2004 |
| WO | WO 2004/064593 A2 | 8/2004 |
| WO | WO 2004/071308 A1 | 8/2004 |
| WO | WO 2004/087240 A1 | 10/2004 |
| WO | WO 2004/098683 A1 | 11/2004 |
| WO | WO 2004/101016 A1 | 11/2004 |
| WO | WO 2004/101071 A2 | 11/2004 |
| WO | WO 2004/110527 A1 | 12/2004 |
| WO | WO 2005/002649 A1 | 1/2005 |
| WO | WO 2005/004973 A1 | 1/2005 |
| WO | WO 2005/018703 A2 | 3/2005 |
| WO | WO 2005/037184 A2 | 4/2005 |
| WO | WO 2005/037350 A2 | 4/2005 |
| WO | WO 2005/039673 A2 | 5/2005 |
| WO | WO 2005/046780 A1 | 5/2005 |
| WO | WO 2005/065748 A1 | 7/2005 |
| WO | WO 2005/068006 A1 | 7/2005 |
| WO | WO 2005/072795 A2 | 8/2005 |
| WO | WO 2005/094920 A1 | 10/2005 |
| WO | WO 2005/118055 A1 | 12/2005 |
| WO | WO 2006/003130 A1 | 1/2006 |
| WO | WO 2006/015507 A2 | 2/2006 |
| WO | WO 2006/015600 A2 | 2/2006 |
| WO | WO 2006/024650 A2 | 3/2006 |
| WO | WO 2006/032689 A1 | 3/2006 |
| WO | WO 2006/032692 A1 | 3/2006 |
| WO | WO 2006/061027 A2 | 6/2006 |
| WO | WO 2006/061354 A1 | 6/2006 |
| WO | WO 2006/062912 A1 | 6/2006 |
| WO | WO 2006/075016 A1 | 7/2006 |
| WO | WO 2006/077262 A1 | 7/2006 |
| WO | WO 2006/077263 A1 | 7/2006 |
| WO | WO 2006/089958 A1 | 8/2006 |
| WO | WO 2006/097111 A2 | 9/2006 |
| WO | WO 2006/108775 A2 | 10/2006 |
| WO | WO 2006/120253 A2 | 11/2006 |
| WO | WO 2006/121921 A2 | 11/2006 |
| WO | WO 2006/122048 A1 | 11/2006 |
| WO | WO 2007/000162 A2 | 1/2007 |
| WO | WO 2007/002523 A2 | 1/2007 |
| WO | WO 2007/02009 A1 | 2/2007 |
| WO | WO 2007/065944 A1 | 6/2007 |
| WO | WO 2007/071255 A1 | 6/2007 |
| WO | WO 2007/071258 A1 | 6/2007 |
| WO | WO 2007/093051 A1 | 8/2007 |
| WO | WO 2007/093182 A2 | 8/2007 |
| WO | WO 2007/122207 A1 | 11/2007 |
| WO | WO 2007/140631 A1 | 12/2007 |
| WO | WO 2007/140783 A2 | 12/2007 |
| WO | WO 2007/140785 A1 | 12/2007 |
| WO | WO 2007/141210 A1 | 12/2007 |
| WO | WO 2008/014791 A1 | 2/2008 |
| WO | WO 2008/014792 A1 | 2/2008 |
| WO | WO 2008/048631 A1 | 4/2008 |
| WO | WO 2008/052545 A1 | 5/2008 |
| WO | WO 2008/092782 A1 | 8/2008 |
| WO | WO 2008/092958 A2 | 8/2008 |
| WO | WO 2008/092959 A1 | 8/2008 |
| WO | WO 2008/135098 A1 | 11/2008 |
| WO | WO 2008/148714 A1 | 12/2008 |
| WO | WO 2008/155145 A1 | 12/2008 |
| WO | WO 2008/155377 A1 | 12/2008 |
| WO | WO 2009/004026 A1 | 1/2009 |
| WO | WO 2009/007287 A1 | 1/2009 |
| WO | WO 2009/010396 A1 | 1/2009 |
| WO | WO 2009/010399 A1 | 1/2009 |
| WO | WO 2009/098291 A1 | 8/2009 |
| WO | WO 2009/098306 A1 | 8/2009 |
| WO | WO 2009/101130 A1 | 8/2009 |
| WO | WO 2009/101145 A1 | 8/2009 |
| WO | WO 2009/103759 A1 | 8/2009 |
| WO | WO 2009/106517 A1 | 8/2009 |
| WO | WO 2009/144272 A1 | 12/2009 |
| WO | WO 2010/003885 A1 | 1/2010 |
| WO | WO 2010/003886 A1 | 1/2010 |
| WO | WO 2010/034830 A1 | 4/2010 |
| WO | WO 2010/072664 A1 | 7/2010 |

OTHER PUBLICATIONS

International Search Report dated Jul. 27, 2005 for International Application No. PCT/DK2005/000189.
International Preliminary Report on Patentability dated Dec. 2, 2005 for International Application No. PCT/DK2005/000189.

* cited by examiner

FIG. 15
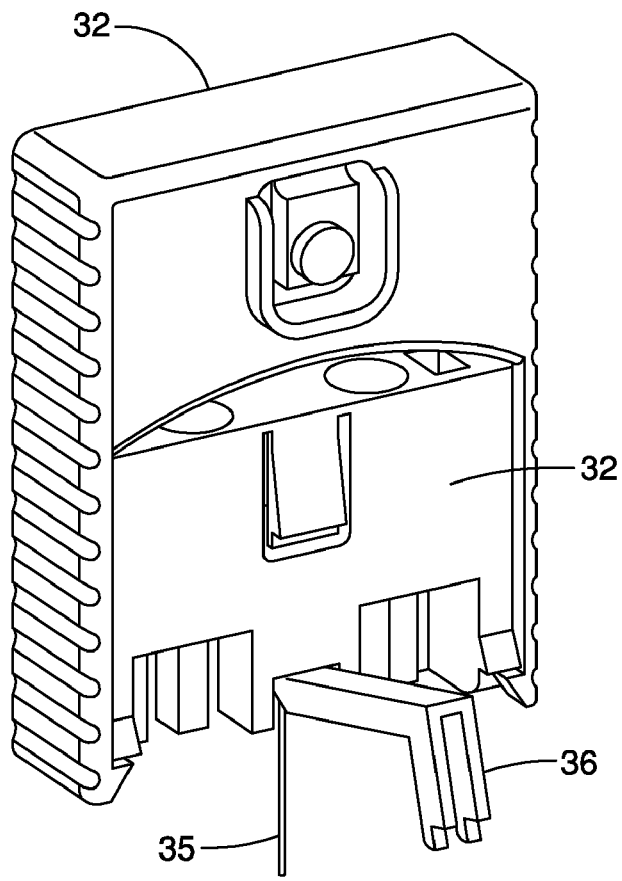
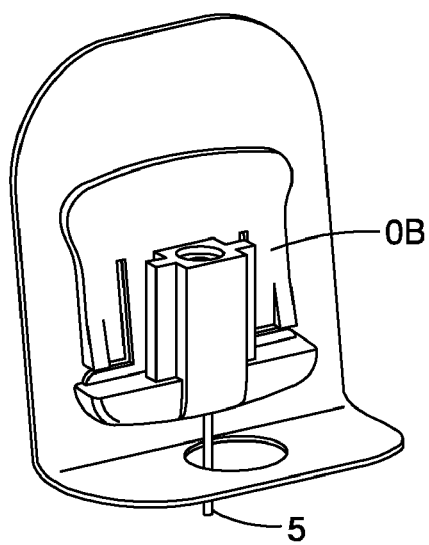

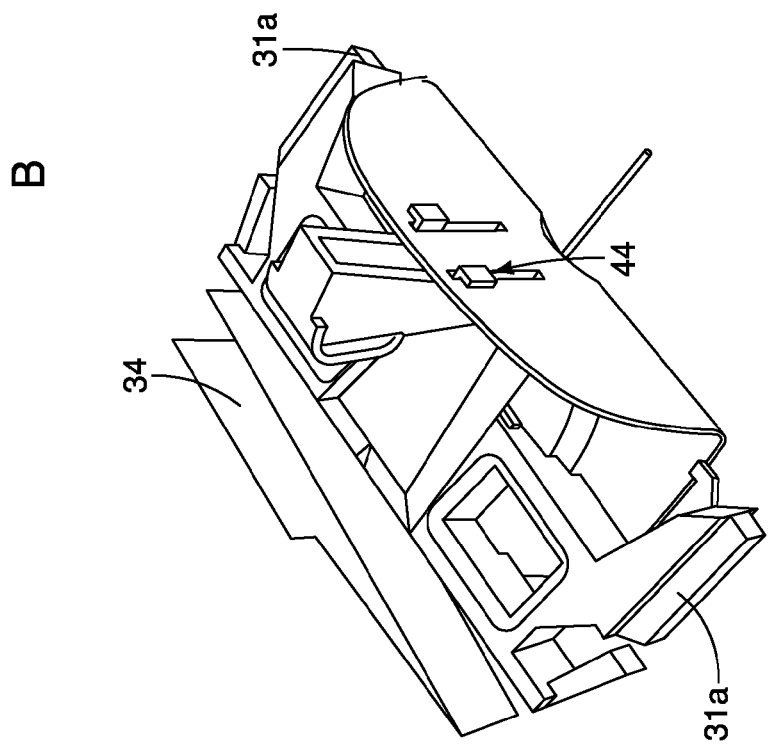
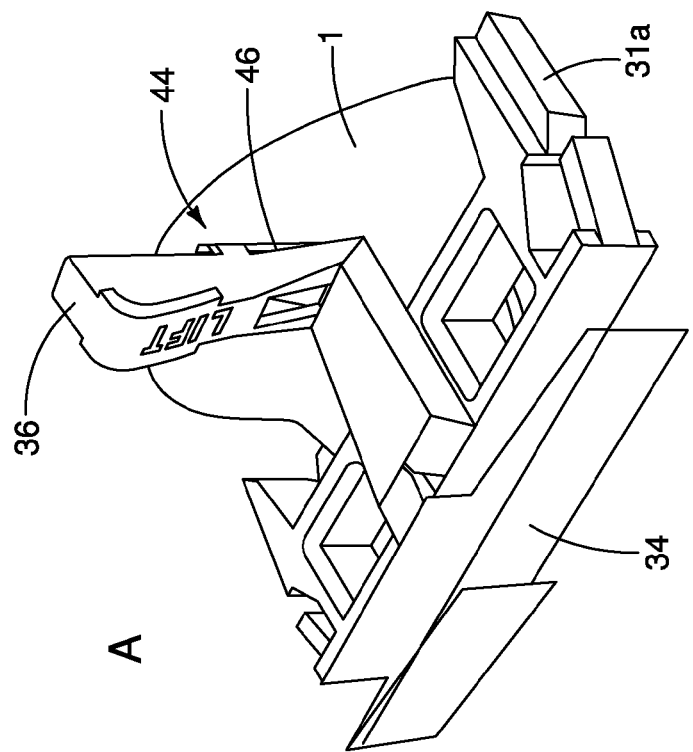
FIG. 23

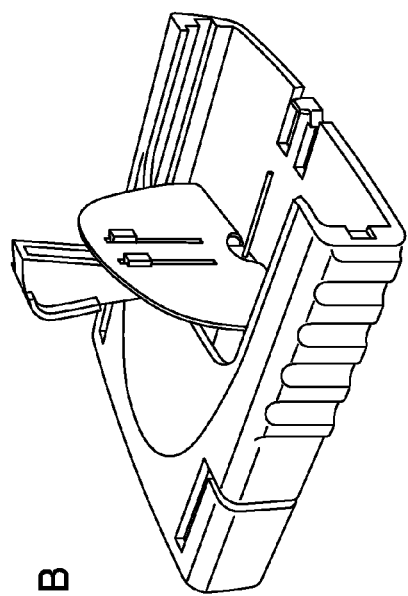
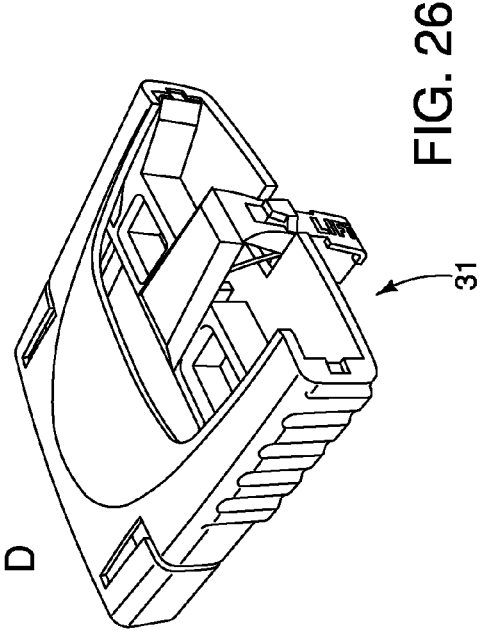
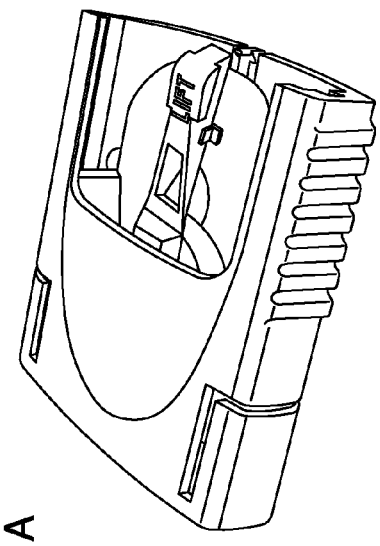
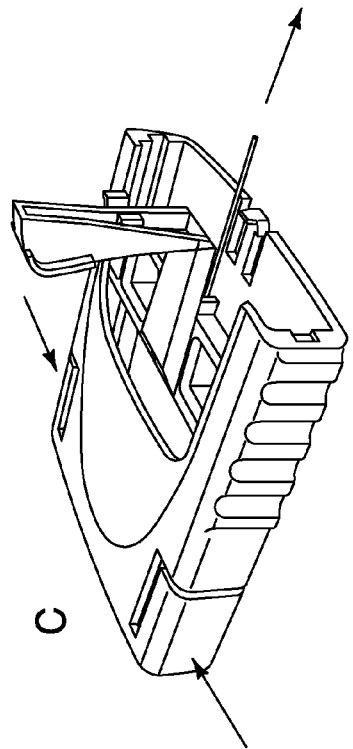
FIG. 26

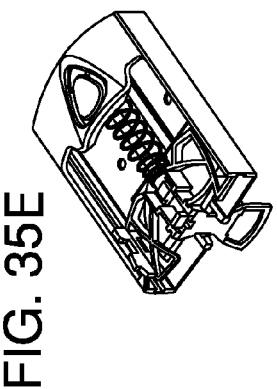
FIG. 35A  FIG. 35B
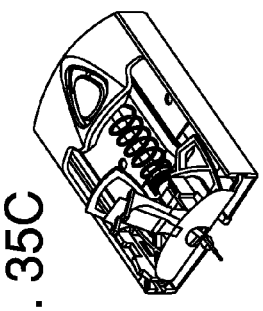
FIG. 35C
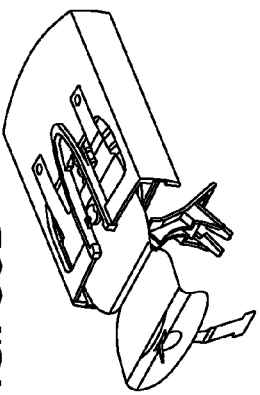
FIG. 35D
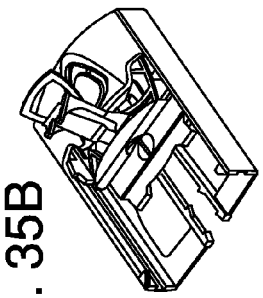
FIG. 35E
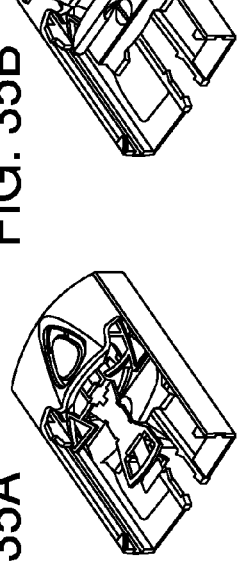
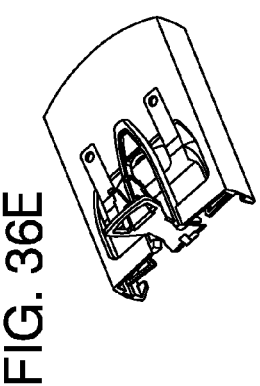
FIG. 36A  FIG. 36B
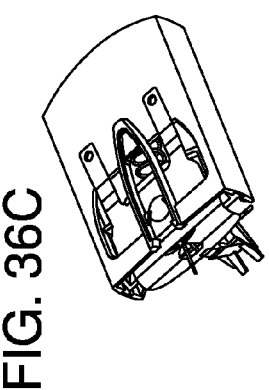
FIG. 36C
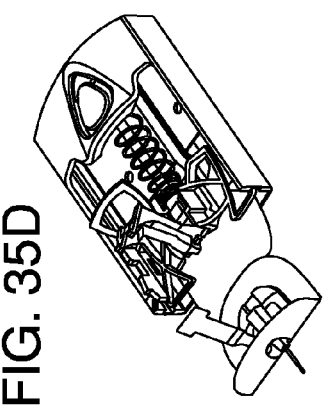
FIG. 36D
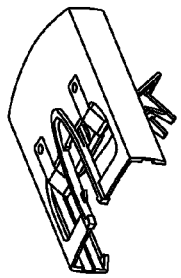
FIG. 36E
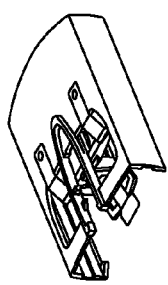

INFUSION SET

This application is a continuation of International Application No. PCT/DK2005/000189, filed Mar. 21, 2005, which claims the benefit of U.S. Provisional Application No. 60/556,863, filed Mar. 26, 2004 and Danish Patent Application No. PA 200400493, filed Mar. 26, 2004, these references are incorporated herein in their entirety.

THE TECHNICAL FIELD

The invention relates to an infusion set for an intermittent or continuous administration of a therapeutical substance, such as insulin. An infusion set comprises an infusion part with a cannula to penetrate the skin of a person and a connector for connecting the infusion part with a medical device preferably a medical delivery device such as an insulin pump.

An infusion set has in its assembled form a substantially planar rear side and a relatively large width compared to its thickness, thus allowing it to lie flat on the patient's skin and thereby minimizing the discomfort of carrying the infusion set.

The infusion part is placed in the patient for a longer and not specified time period while the connector is supposed to be connected and disconnected from time to time. Hereby it is possible for the patient to disconnect from the medical device, move around and at a later point re-connect to the medical device. Further it is possible to shift between different medical devices using the same infusion part and thereby there is only need for one penetration of the skin which provides less discomfort to the patient.

PRIOR ART

U.S. Pat. No. 5,522,803 discloses an infusion set having an infusion part and a connector. The infusion part comprises a soft plastic cannula in liquid communication with a cavity for receiving a needle from a connector, two sloping guiding holes and two retention devices; and the connector comprises a cannula, two square guiding pins and two arms with a hooking part for gripping the retention device of the infusion part and operating in the main plane of the infusion part.

U.S. Pat. No. 6,572,586 discloses an infusion set for administration of a fluid to a subcutaneous layer and include a cannula housing adapted for mounting onto a patient's skin and a needle housing for connection to the cannula housing. The needle housing has a pair of flexible and a resilient band connected to the sidewalls. The resilient band is lockably engage able with the cannula housing thereby securing the housings together, and the resilient band is releasable from the cannula housing when pressing the sidewalls toward each other to deform the resilient band. A hollow needle extends out of a main body of the needle housing for delivering fluid to the cannula from a fluid source. The walls of the needle housing extend beyond a distal end of the hollow needle to prevent needle contact with contaminated surfaces an inadvertent injury.

In both of these infusion sets two arms are formed along the sides of the connector part and the movement performed to unrelease the connector from the infusion part is in both cases pressing the two arms together. Compared to these to constructions the present invention is of a more simple form and also the locking mechanism according to the invention allows for the user to actually see when the arms are unlocked, especially if the infusion part and the connector are toned in different colors.

Given that the infusion part is supposed to be connected and especially disconnected several times with the connector it is important that this operation is painless and simple to perform.

The object of the invention is to provide an infusion set with a coupling mechanism which can be connected and separated with as less discomfort to the patient as possible, and which infusion set is also easy for the patient to find out and to operate.

According to the invention there is provided an infusion set comprising an infusion part for insertion into a patient and a connector for connecting the infusion part with a medical device through a tube. The connector is axially displaceable relative to the infusion part, said infusion part comprising an adhesive support, a base part with a first set of guiding means and at least two retention devices for locking the connector to the infusion part, a cannula extending from said base part and being in fluid communication with a cavity which is optionally covered with a membrane, said cavity being further adapted to receive a second cannula extending from the connector, which second cannula is in fluid communication with the tube, a second set of guiding means adapted to fit with the first set of guiding means and at least two arms where the retention devices are extending from the upper surface of the main surface of the base part and the arms comprise means corresponding to the retention means.

The above described infusion set is easier to disconnect and will seem safer to use for the patient than previously known infusion sets. All that is needed to separate the connector from the infusion part is a slight simultaneous pressure on the two arms of the connector and the user will be able to see how the connection/disconnection between the infusion part and the connector takes place.

With the term cavity is meant the inner lumen of the cannula or the extension of the cannula.

In a preferred embodiment the connector is symmetrical both around the main plain of the connector and around the plane being perpendicular to the main plane and being parallel to the central axis, thus allowing the connector to be connected to the infusion part no matter which of the main sides is facing upwards. This results in an easier operation of the infusion set.

The arms of the connector can appropriately be provided with gripping means for getting a better grip of the connector. Examples of such gripping means could be but are not limited to rims, grooves, recesses, and a roughened surface optionally of another material than the connector itself, preferably recesses are used. This results in a safer and more comforting operation of the infusion set since the risk that the fingers slip during handling resulting in unintended movements of the infusion part and the cannula is reduced.

In one embodiment of the invention the connector has a reduced material content e.g. in the form of at least one groove, preferably at least two grooves, placed where the arms are connected to the central part of the connector comprising the second set of guiding means (8), thus allowing the arms of the connector to move perpendicular to the base part while the second set of guiding means are stationary. This makes it possible to disconnect the connector from the infusion part by lifting the arms instead of pressing them towards each other. Hereby it is achieved that connection/disconnection can be performed in a manner which at the same time reduces the stresses in the material during the operation, eases the operation of the locking mechanism and reduces the patient's unpleasantness during the connection/release of the connector.

In another embodiment retention devices are positioned on a particularly flexible part of the base part. The flexible part can be provided by choosing an appropriate material for the base part or by providing very thin parts of material between the retention parts and the center of the base part, but preferably the base part of the infusion part has at least two cuttings forming at least two flaps. The formed flexible parts are able to in an elastic manner to move out of the main plane of the infusion part. Hereby the same advantages during connection/release as described above are obtained.

In a preferred embodiment the cannula of the infusion part penetrates the adhesive support, thus stabilizing the position of the infusion part relative to the point of skin penetration to an even greater extend. Further this minimizes the risk that the cannula is accidently withdrawn from the patient.

In a preferred embodiment the adhesive support is a plaster.

In a preferred embodiment the infusion part and the connector are made from two different plastics materials, such as two different types of polypropylene.

In a preferred embodiment there is a visual difference in the toning of the connector and the base part of the infusion part. Hereby it is achieved that it is easier for the patient to see the separation line between the two units resulting in an easier operation of the locking mechanism.

In a preferred embodiment the retention devices are in form of at least two steps placed on either the infusion part or the connector and a matching carving in the other part. Preferably the step has a side with a triangular shape thus forming the step as a sloping hill. Preferably the retention devices are placed on the infusion part and the matching carvings are placed in the connector's arms.

In a preferred embodiment the tube is a flexible plastics material which preferably is connected with the rest of the connector by means of glue.

Preferably the medical delivery device is a drug delivery device such as an insulin delivery device e.g. in the form of an insulin pump.

The cannula of the connector can be a hard cannula, preferably a metal cannula such as a steel cannula. Also the cannula of the connector can be made of a plastics material and/or being blunt.

In a preferred embodiment the cannula is a soft cannula preferably a soft cannula made of a plastics material. Preferred plastics materials for the soft cannula are materials which are sufficiently flexible to bend, when the patient moves and sufficiently rigid to avoid kinking, closing off the drug supply. Further the material must be compatible with medical use i.e. irritation of the skin must be kept at a minimum, being non-toxic it must not decompose in the body, etc. Thermoplastic elastomers (TPE) are a type of material which fulfils these requirements. Examples of such useful elastomers are: polyester ethers, ECDEL, styrene based TPE, olefin based TPE, urethane based TPE, ester based TPE, amid based TPE, polyolefins and silicone rubbers. In a preferred embodiment the material is selected from the group consisting of polypropylene, C-FLEX™, mixtures of C-FLEX™ and polypropylene, LUPOLEN™ 1840H, LUPOLEN™ 3020D, PELLETHANE™ 2363-75D, PELLETHANE™ 2363-55D, TECOTHANE™ and CARBOTHANE™.

In a preferred embodiment the infusion part and the connector are made of polypropylene.

Given that the infusion part is supposed to be connected and especially disconnected several times with the connector it is important that the cannula of the connector is guided safely into the cavity of the infusion part and that the cannula in the disconnected situation is protected as much as possible. It is therefore a further object of the invention to provide an infusion set with an improved guiding mechanism and with an improved protection of the connector cannula.

In a preferred embodiment the connector cannula is extending from the central part of the connector and being placed in a withdrawn position relative to the front of the central part and at least one of the first set of guiding means comprises at least two stabilizing fins.

The above described invention provides an infusion set with an improved protection of the cannula of the connector thus allowing the connector to be connected and disconnected from the infusion part more times than in the previously known infusion sets.

A lot of patients e.g. insulin patients have to or may desire to insert an infusion device or to place a subcutaneous sensor or the like themselves. For some persons it is a troublesome process to perform the skin penetration themselves, they therefore need a device which assists them in this process thereby making the process less problematic.

The document US 2003/0225373 discloses an insertion device for inserting an infusion part or a sensor into a patient. The device comprises a housing, a coil spring, a safety device and part for angling the insertion into the patient. However the apparatus is relatively complicated to manufacture industrially and further the device has to be loaded manually by the patient by a rather complicated procedure.

WO 03/026728 A1 discloses an injector device comprising a housing, a spring, a slidable bar, a locking mechanism and a needle.

It is a further object of the invention to provide an improved insertion device which is easy to manufacture and which is suitable for being delivered in a loaded form or at least being easier to load. Especially elderly people who can have some motor problems need an insertion device which exists in a pre-loaded form.

The advantage in essentially vertical insertion is that it is easier to control the dept of the needle penetration and thereby the dept of the cannula. This is important in self-insertion of the infusion part.

In the following the invention will be described in further details with reference to the figures.

FIG. 15 shows the second embodiment of the injector device after separating the injector from the infusion part.

FIG. 21A-D shows assembling of the infusion part and injector device according to the third embodiment.

Figure 22:
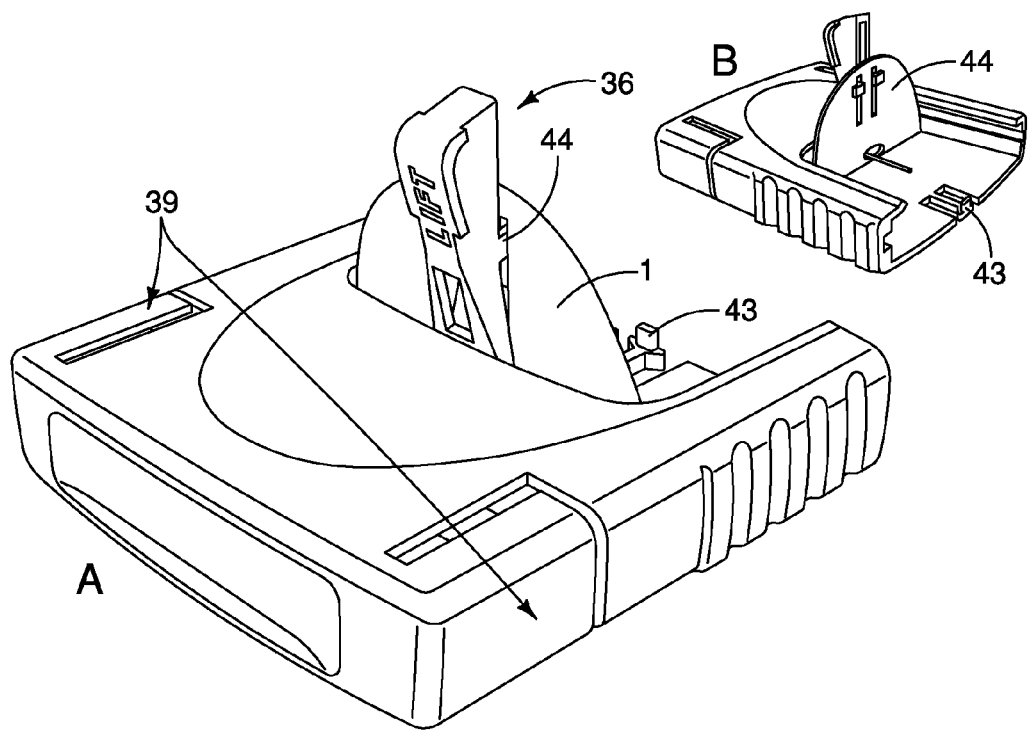

FIG. 22 A-B shows the third embodiment of the injector device prepared for insertion.

FIG. 23 A-B shows the adhesive support of the infusion part hooked to the slidable member.

Figure 24:
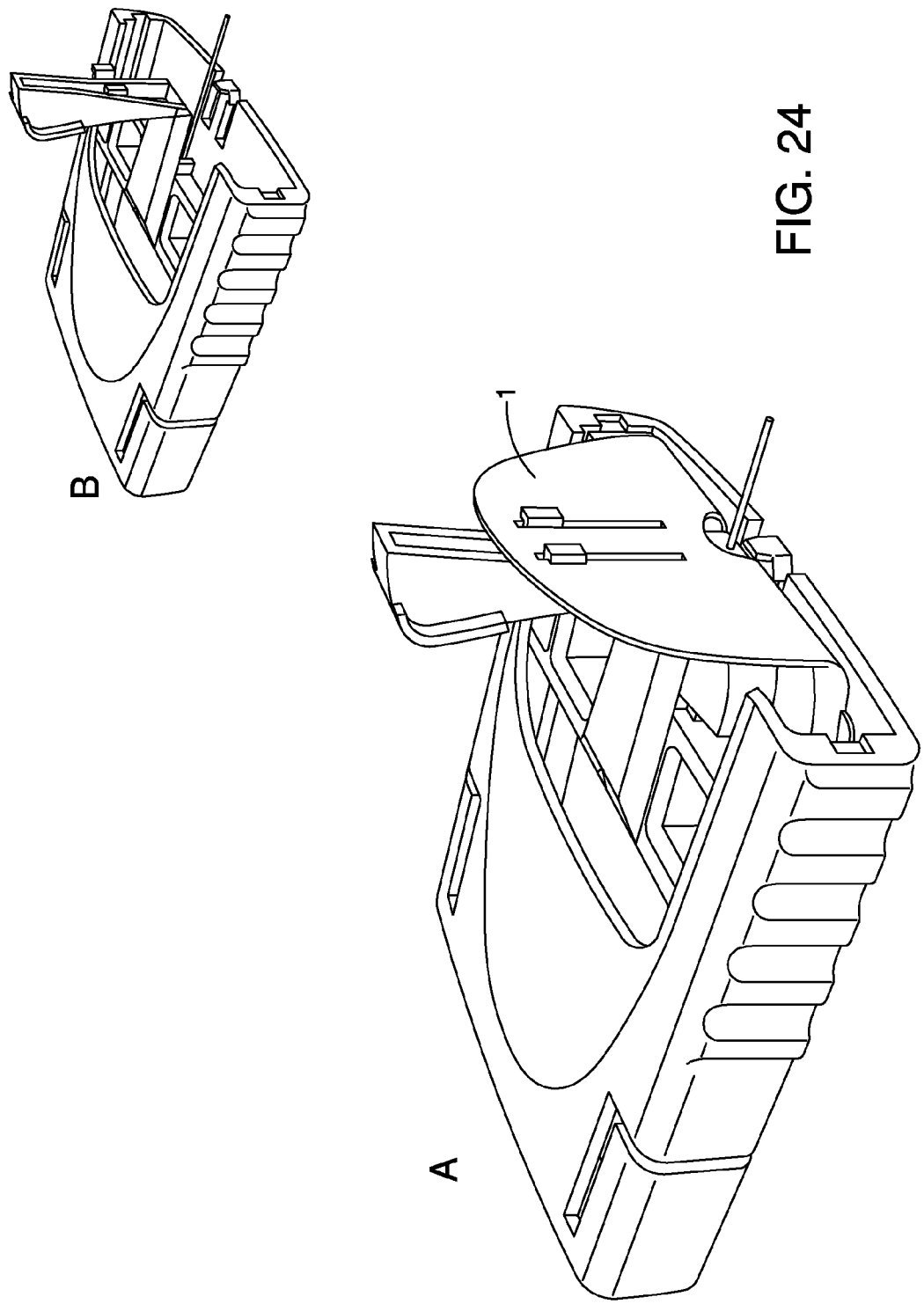

FIG. 24 A shows the injector device after insertion with an infusion part and FIG. 24 B shows the injector device after insertion without the infusion part.

Figure 25:
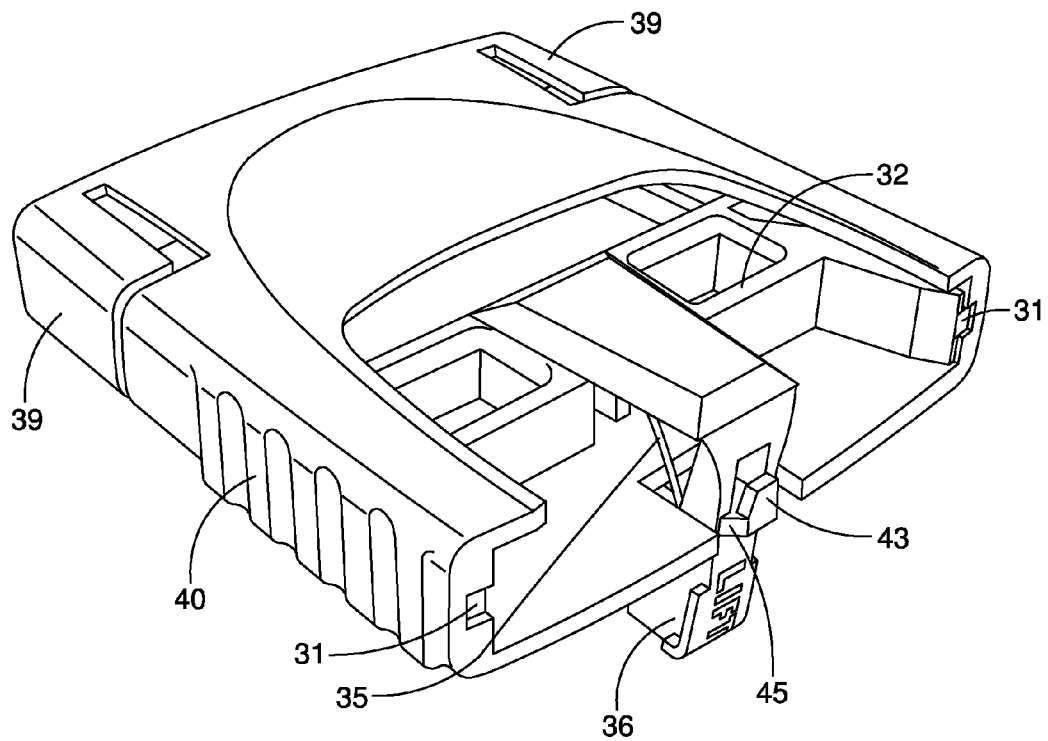

FIG. 25 shows the third embodiment of the injector device after insertion and embracing the needle.

FIG. 26 shows a third embodiment of an infusion part placed on a mounting pad with two separate pieces of release liner.

FIGS. 35 A-E and 36 A-E show the different steps when using the injector device for injecting the infusion part.

Figure 1:
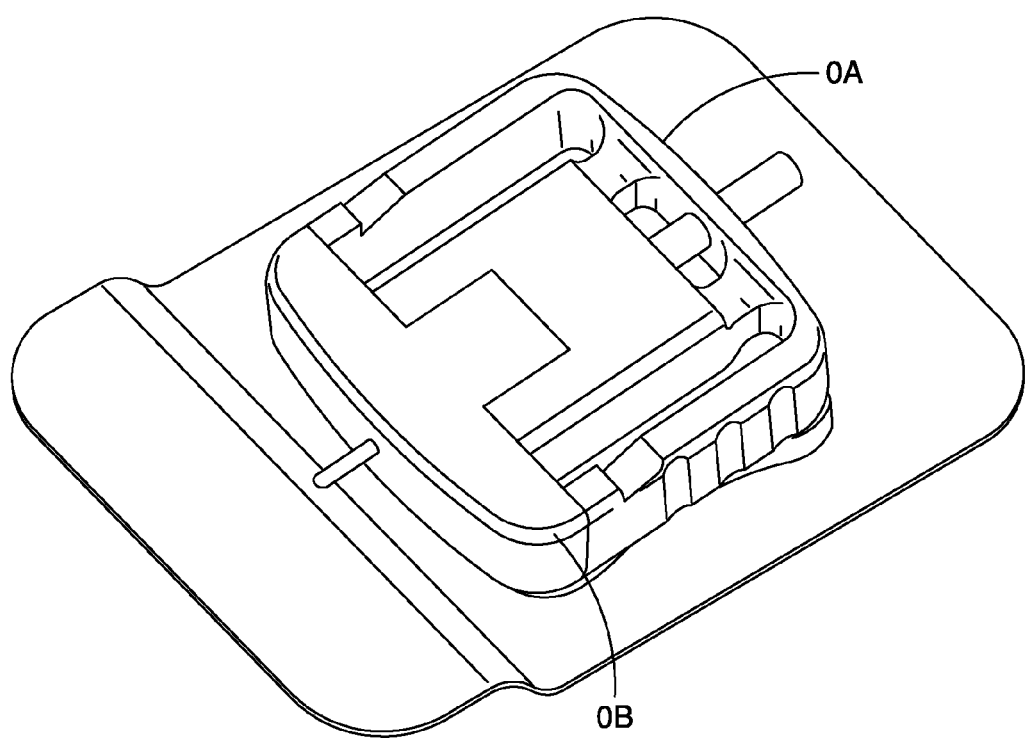
FIG. 1 shows one embodiment of an infusion set where the infusion part and the connector are unified.
Figure 2:
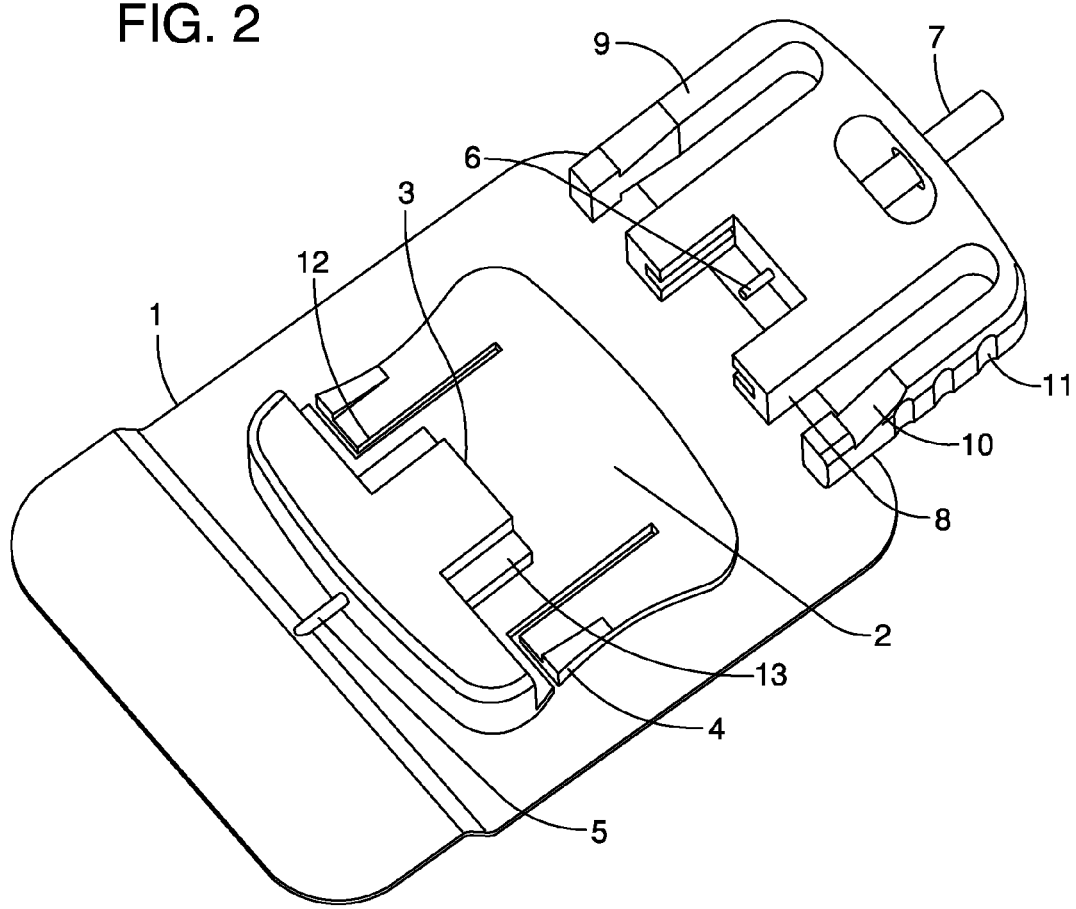
FIG. 2 shows one embodiment of the infusion set where the infusion part and the connector are separated.
Figure 3:
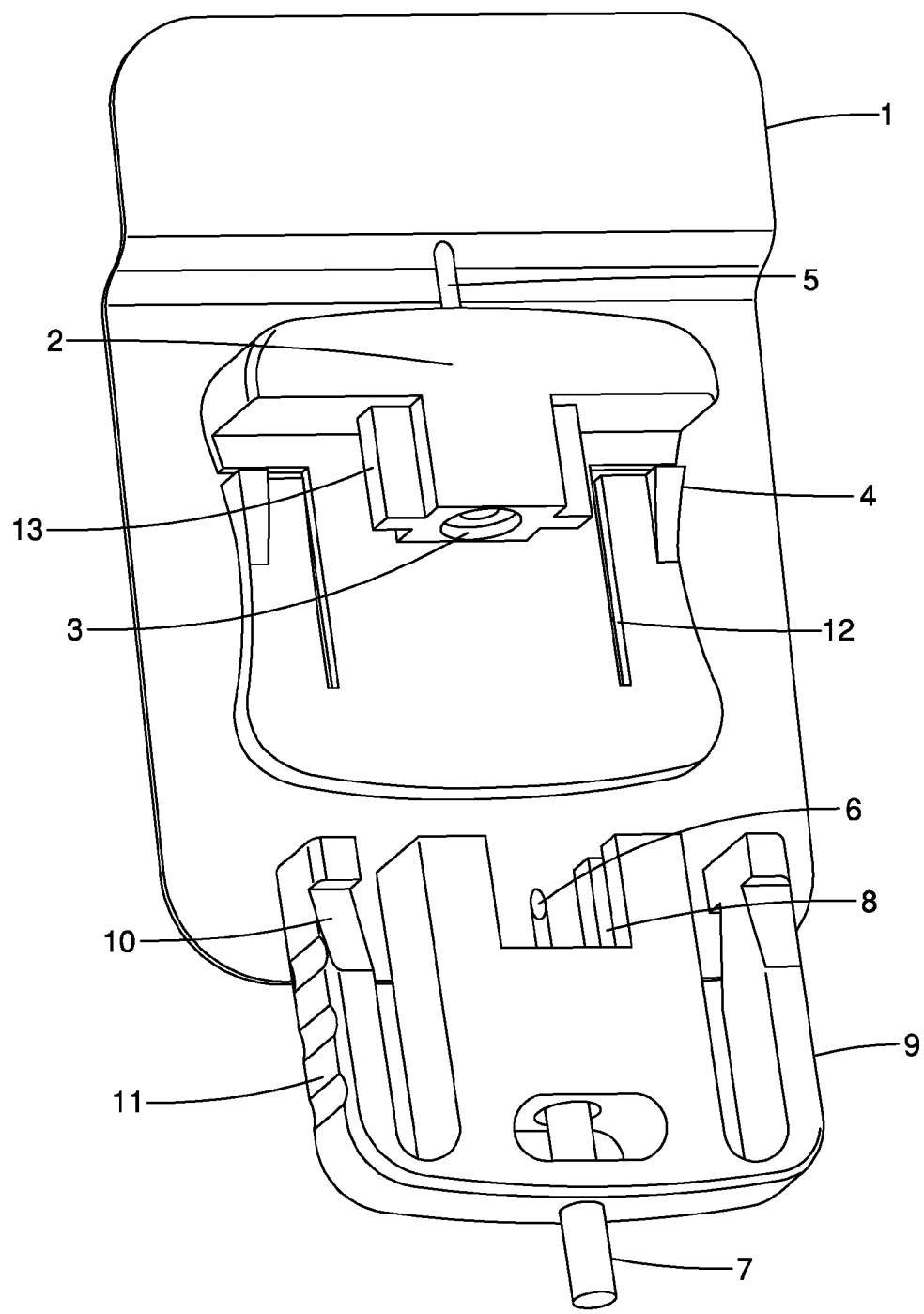
FIG. 3 shows the same embodiment of the separated infusion set as in FIG. 2 from a different angle.

FIGS. 1-3 illustrates an embodiment of an infusion set. The infusion set comprises an infusion part (0B) and a connector (0A). The infusion part (0B) comprises a base part (2) having a main plane which, when the infusion set is attached to a patient, is essentially parallel to the skin of the patient, and a shoulder part (2a) protecting the connector part (0A) from being released unintentionally. Said base part (2) comprises a first set of guiding means (13) which in this case has the form of two stabilizing fins. The base part further comprises two retention devices (4) extending from the upper surface of the base part in this case in form of two steps. Mounted on the inner surface of the infusion part is an adhesive support (1) which in this case is a plaster. A cannula (5) is extending from the base part (2) and is penetrating the adhesive support (1) being in fluid communication with a central cavity (3). The cannula (5) is preferably a soft cannula but could also be made of metal. The cavity (3) optionally being covered by a membrane is adapted to receive a second cannula (6) extending from the connector. In the embodiment shown in FIGS. 2-5 the second cannula (6) is extending from the central part of the connector and is placed in a retracted position relative to the front of the central part. In this embodiment the base part (2) has two cuttings (12) creating two flaps on which the retention devices (4) are mounted. The connector (0A) comprises two arms (9) having four carvings (10) adapted to fit with the retention devices (4). The connector (0A) is symmetrical around the main plane and around the plane perpendicular to the main plane and parallel to the main axis thus allowing the connector to match with the base part in two ways. The cannula (6) is in fluid communication with the tube (7) which provides the connection to a medical device such as an insulin pump. In this embodiment the central part of the connector has a second set of guiding means (8) in form of two grooves placed symmetrically around the main plane of the connector. In this embodiment the connector further has gripping means (11) in form of recesses. The gripping means

Figure 4:
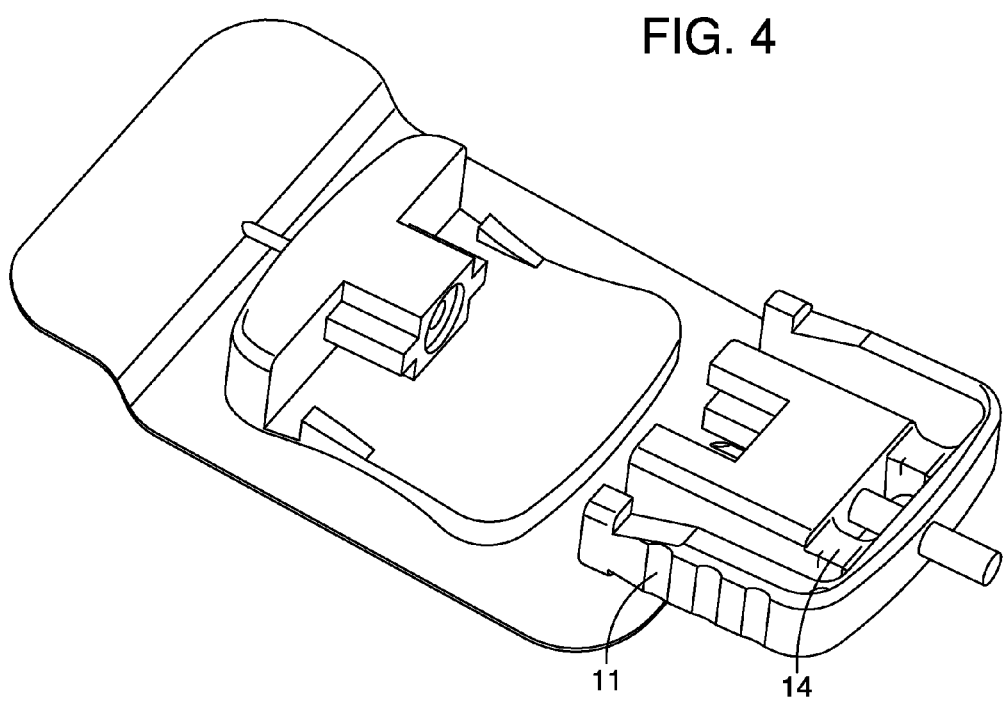
FIG. 4 shows a second embodiment of a separated infusion set from a first angle.
Figure 5:
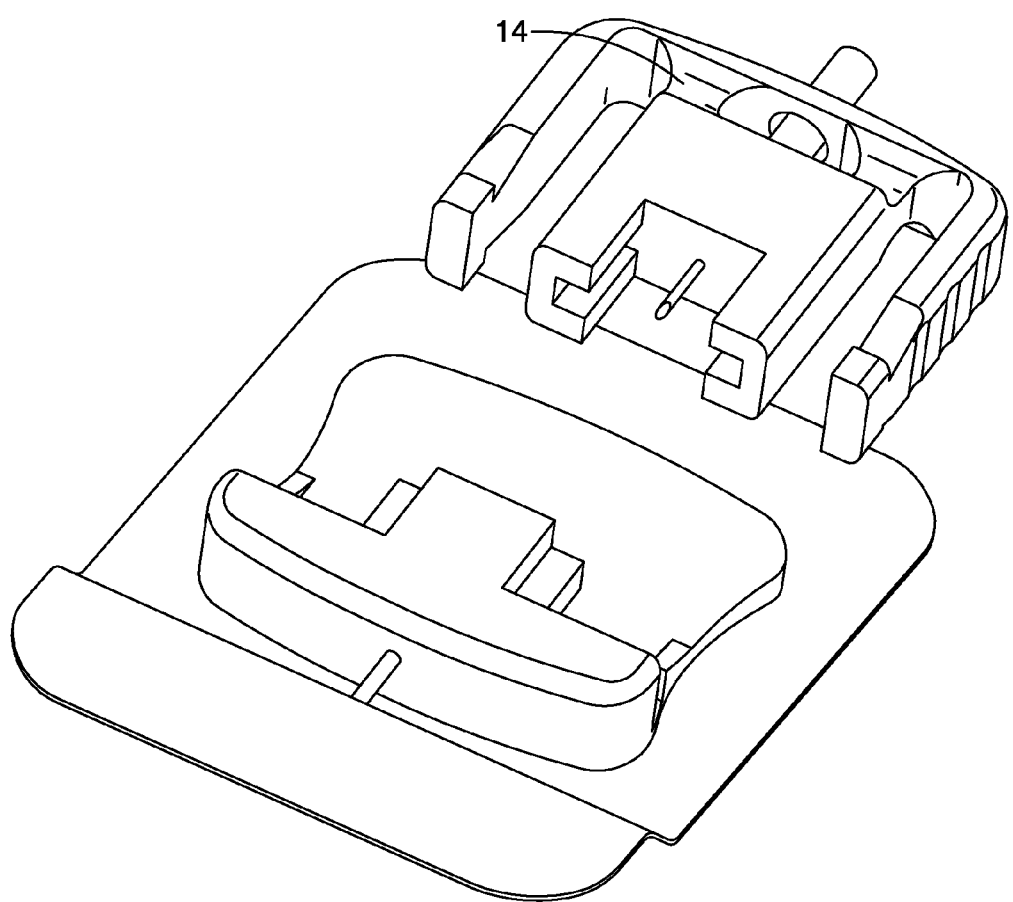
FIG. 5 shows the second embodiment of the infusion set from a different angle.

11 are optional and can be selected from the group consisting of rims, grooves, recesses or a roughened surface optionally of another material than the connector itself FIGS. 4 and 5 show another embodiment of the invention where the connector has two grooves (14) which in this case are placed symmetrically around the main plane of the connector. However it is not necessary for the grooves to be places symmetrically around the main plane since they are not coupling with the infusion part.

Whether the infusion set is intended to be inserted manually or by an injector the infusion part (0B) and the connector (0A) are delivered to the user as two separate units in sterile packages. When inserted manually the infusion part (0B) will at delivery be combined with a needle unit with the same locking and guiding means (8) as the connector. The needle unit is provided with an insertion needle extending from the central front which insertion needle at delivery extends through and beyond the end of the cannula (5). The needle unit's only function will be to penetrate the user's skin where after the needle unit is removed and replaced with the connector (0A) leaving the cannula (5) subcutaneous.

The connector (0A) can be connected to a luer coupling member through the tube (7). Through the luer coupling it is possible to administer a suitable therapeutical substance, such as insulin from a pump. The connector can also be a sort of closing part with a suitable entrance for an inserting needle of a syringe. Such a closing part can stay in position for up till three days while the user can have medication, e.g. insulin injected through the entrance in order to reduce trauma to the skin caused by repeated penetration of the skin.

It is important for the user that it is easy to change i.e. to engage and to disengage the infusion part (0B) and the connector (0A) even when the user has reduced dexterity. The present invention complies with this purpose as the movement used to unlock the infusion part (0B) from the connector (0A) is pressing the connector between the first finger and the thumb which is simple and easily performed movement. Also the oppositely directed forces from respectively the first finger and the thumb pushing toward each other, are not only used to unlock the device but is also used when pulling the connector away from the infusion part (0B). In order to make it easier to disengage the connector (0A) the arms (9) can be made very flexible, either by choosing a soft and flexible material or by making the fastening of the arms (9) to the central part more or less rigid e.g. by varying the size of the grooves (14) on the shoulder of the connector (0A).

Although the arms (9) are very flexible the danger of accidently pulling the connector away from the infusion part when positioned on the skin of the user is quite small as the device has to be exposed to a simultaneous pressure from both sides.

Another advantage of the invention according to the present invention is that only a very small amount of material need to be used when producing the infusion part. The infusion part (0B) can be reduced to:

a slim central part comprising the cannula (5), the cavity (3) and guiding means (13), a shoulder part (2a) connected to the central part and protecting the ends of the movable arms (9) of the connector when the connector is engaged with the infusion part, and a base part (2) which has been reduced to two arms connected to the central part which arms are provided with the retention means (4).

Figure 6:
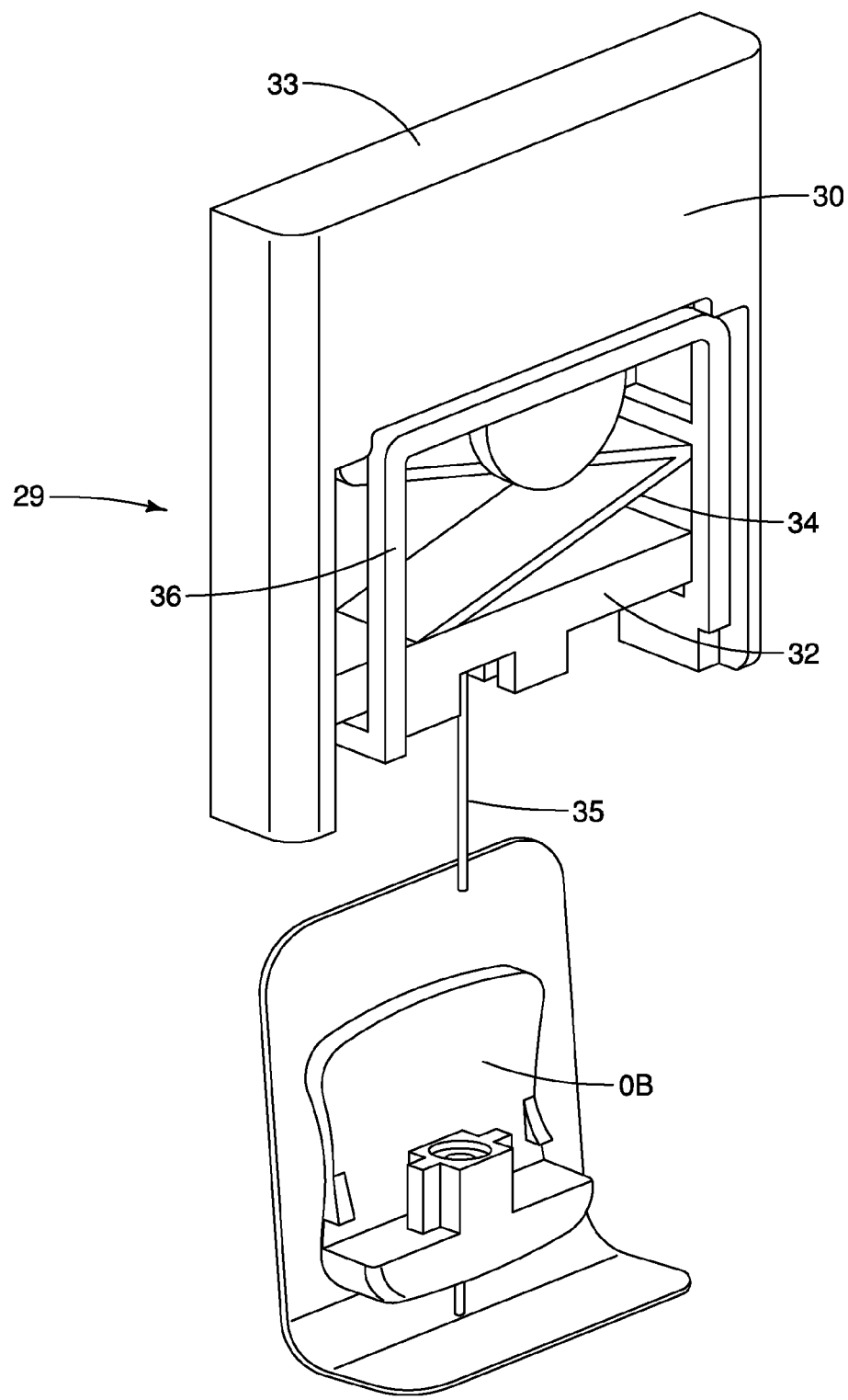
FIG. 6 shows a first embodiment of an injector device separated from the infusion part.
Figure 7:
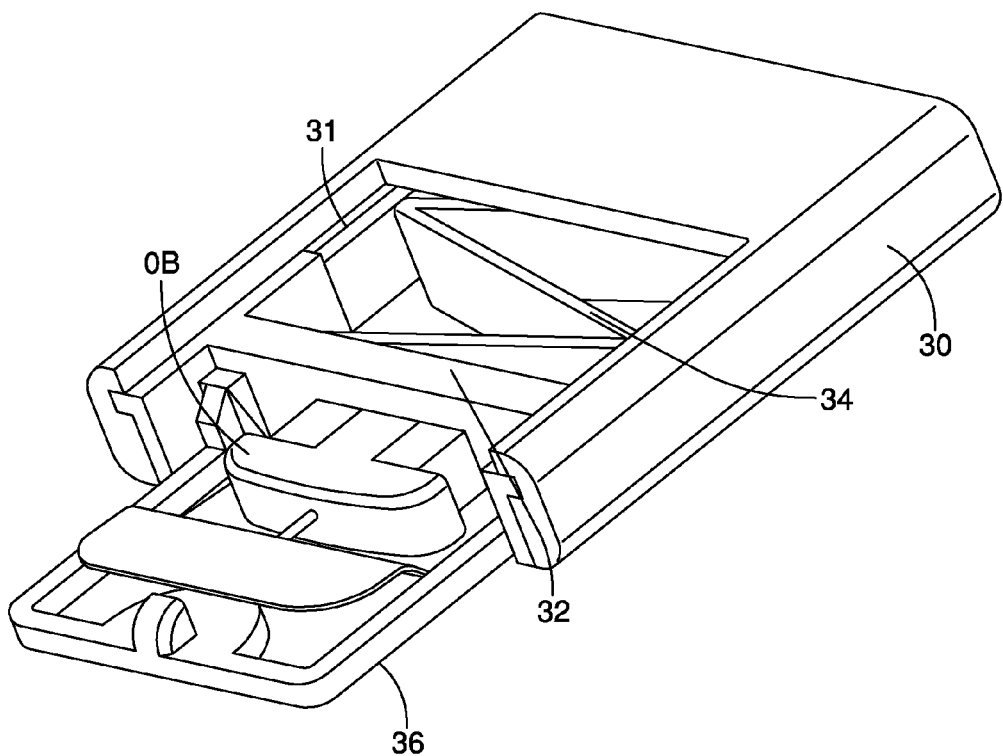
FIG. 7 shows the first embodiment of the injector device joined with the infusion part.
Figure 8:
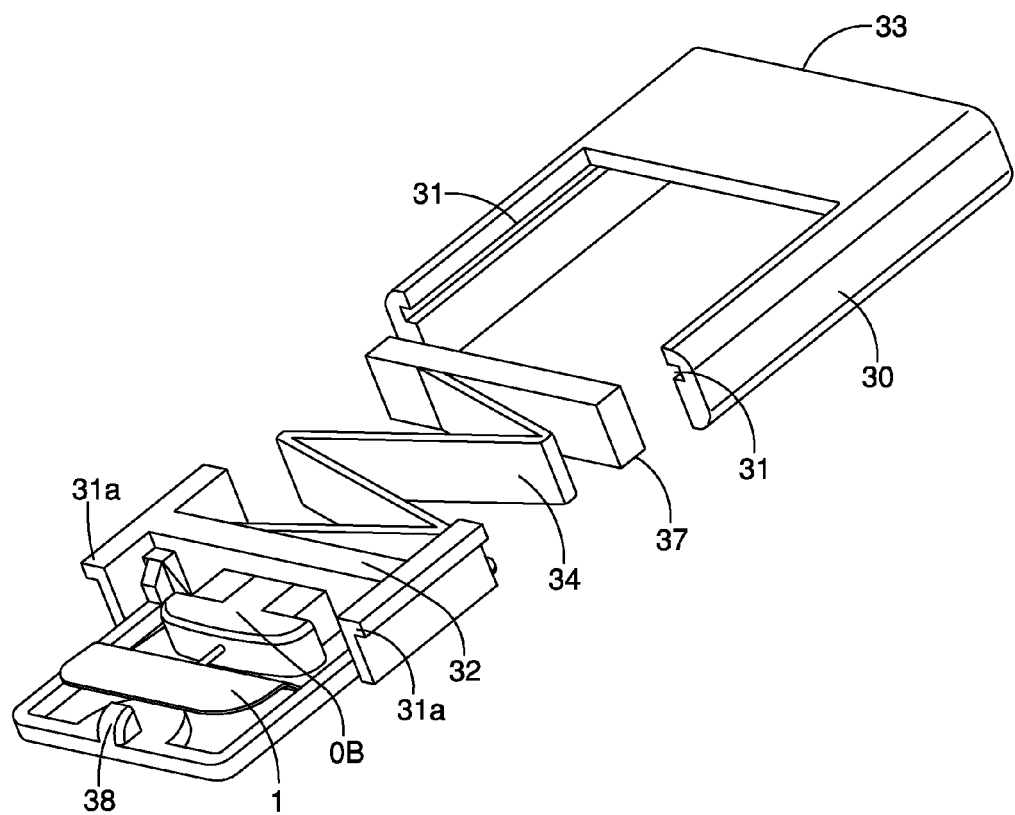
FIG. 8 shows the first embodiment of the injector device joined with the infusion part.
Figure 9:
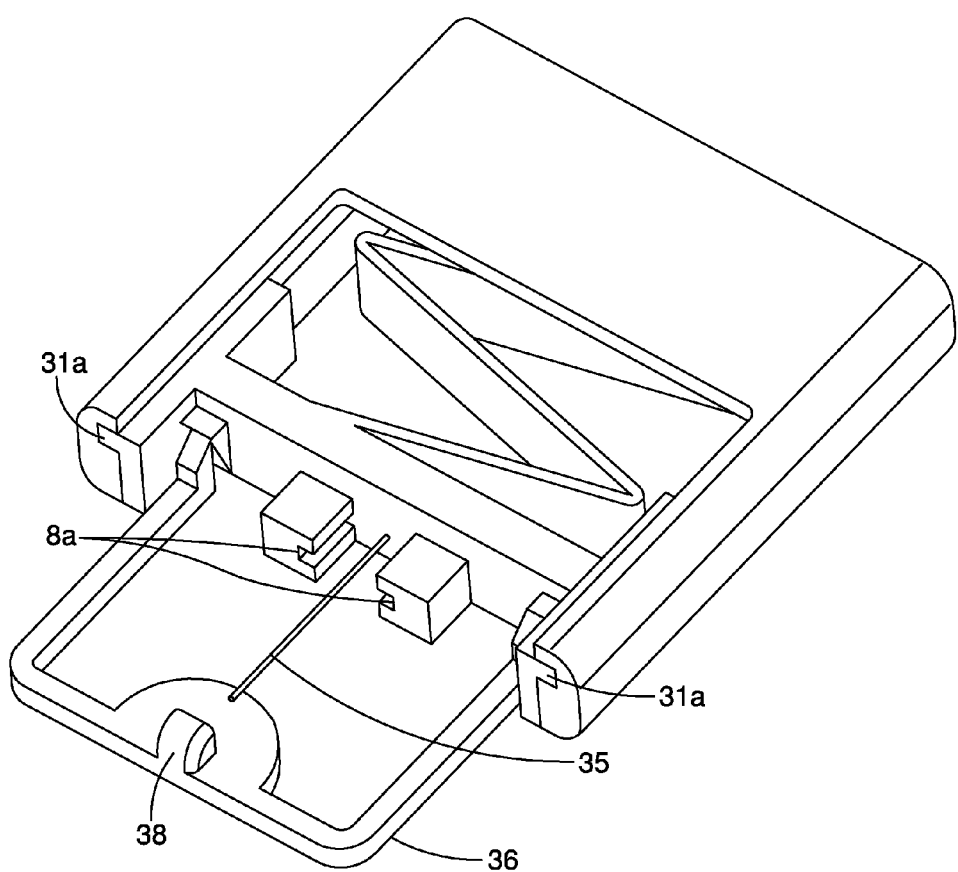
FIG. 9 shows the first embodiment of the injector device where the pivoting member is embracing the needle.

FIGS. 6-11 shows a first embodiment of an injector device (29) which can be used for injection of the infusion part (0B) of the infusion set. In FIG. 6 the injector device is separated from the infusion part (0B) and FIGS. 7 and 8 show the same injector device (29) joined with an infusion part (0B). The injector device comprises a housing (30) with two longitudinally extending guiding means (31) formed as grooves in this embodiment and a longitudinally slidable member (32) having guiding means (31a), in this embodiment a rim, corresponding to the guiding means (31). A penetrating needle (35) is extending from the front part of the slidable member (32), and the needle (35) is at the end where it is fastened to the slidable member (32) surrounded by guiding means corresponding to the guiding means (13) on the infusion part (0B). The slidable member (32) is capable of moving from a retracted position to a forward position, and is driven from the retracted position to the forward position by a spring (34). The spring is located between the slidable member (32) and the back (33) of the housing. Optionally there is a spring support (37) (FIG. 8) which fits with the back of the housing thereby minimizing the risk of a malfunctioning spring. The injector device further comprises locking means (38) for maintaining the spring in a compressed state and release means (39) for disengaging the locking means. When the locking means (38) are disengaged, the spring (34) drives the slidable member (32) to its forward position, thus introducing the cannula positioned at the front end of the infusion part (0B) into the patient by means of the needle (35). After the introduction of the cannula, the injector device including the insertion needle (35) is withdrawn from the infusion part (0B) leaving the insertion needle in an exposed position. The pivoting member (36) can then be swung into a position where it embraces the needle (35) as shown in FIG. 9.

Figure 10:
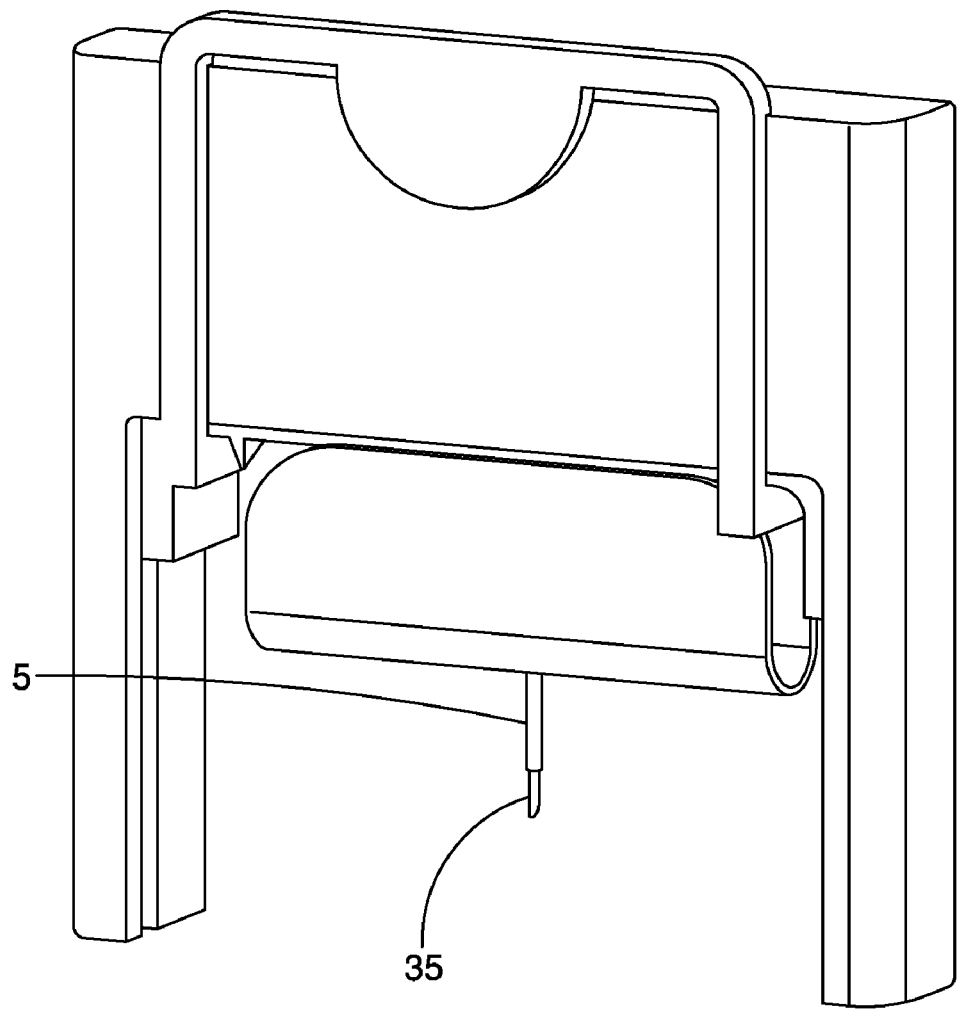
FIG. 10 shows the first embodiment of the injector device in the loaded position.
Figure 11:
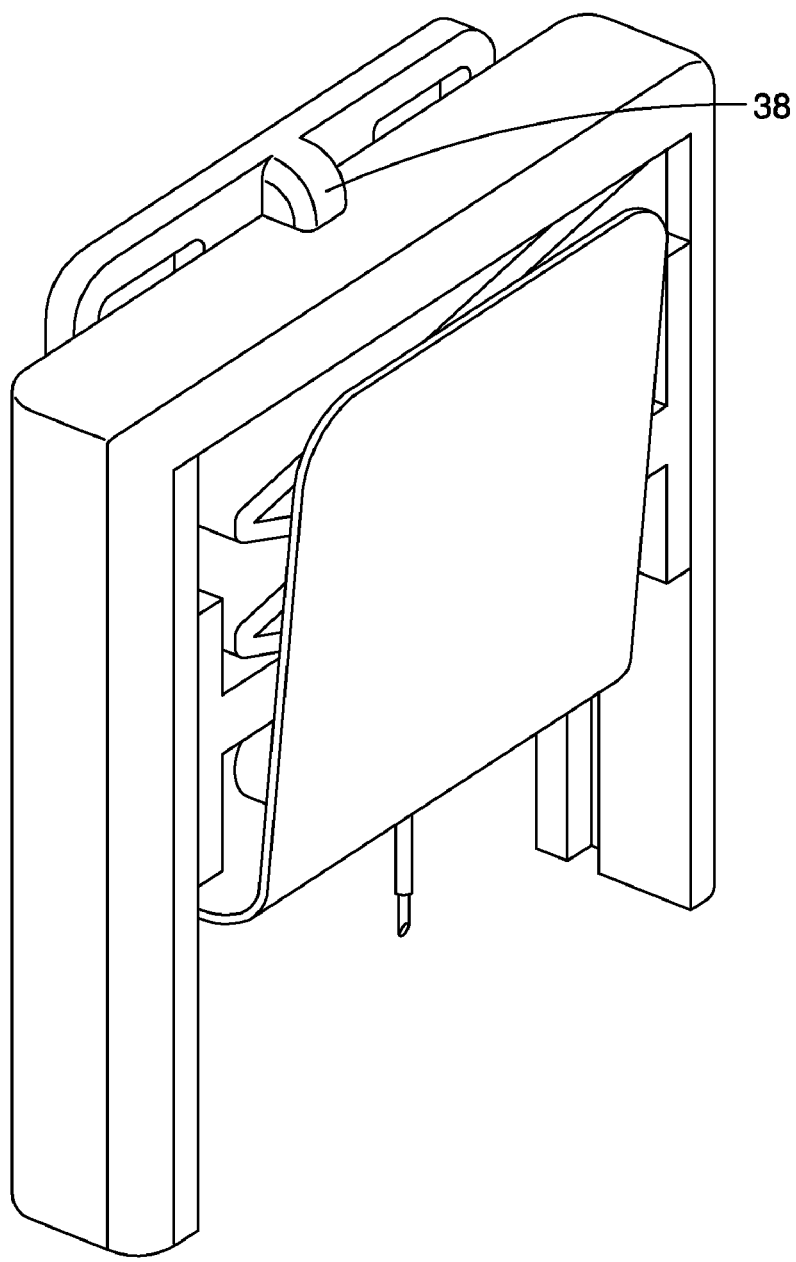
FIG. 11 shows the first embodiment of the injector device in the loaded position from a second angle.

FIG. 10 and FIG. 11 show the same embodiment of the injector device in a loaded and secured position. Part of the pivoting member (36) acts as locking means (38). In FIG. 10 it can be seen how the needle (35) fits into the cannula (5) of the infusion part. The needle (35) will bring the cannula (5) with it during the skin penetration. After penetrating the skin the needle (35) secured to the injector will be withdrawn leaving the cannula inserted in the patient. In FIG. 11 the locking means are shown said locking means are disengaged when the tab (38) is pushed over the edge of the outer side of the back (33) of the housing.

Figure 12:
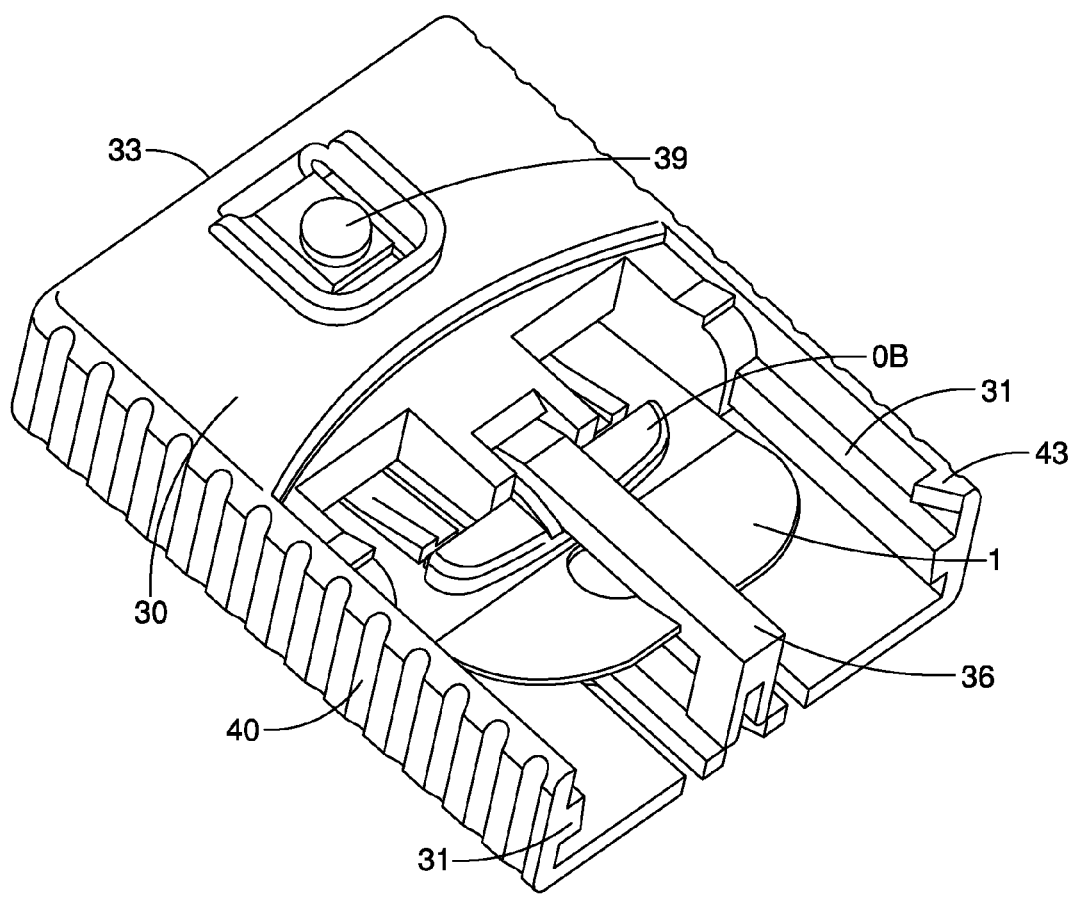
FIG. 12 shows a second embodiment of the injector device in a loaded and secured state.

FIGS. 12 to 17 show a second embodiment of the injector device according to the invention where the pivoting member (36) is fastened centrally in relation to the slidable member (32). FIG. 12 shows the injector device in a state where the pivoting member (36) protects the needle prior to injection of the cannula (5) of the infusion part (OB). The figure shows the housing (30) with another type of longitudinally extending guiding means (31), in this case a bar. The housing further has gripping means (40), preferably in the form of recesses, as means for getting a better grip of the injector device.

Centrally positioned release means (39) is shown on one of the main faces of the injector device. The advantage of a one button release mechanism is that the risk of a slanting injection is reduced.

Figure 13:
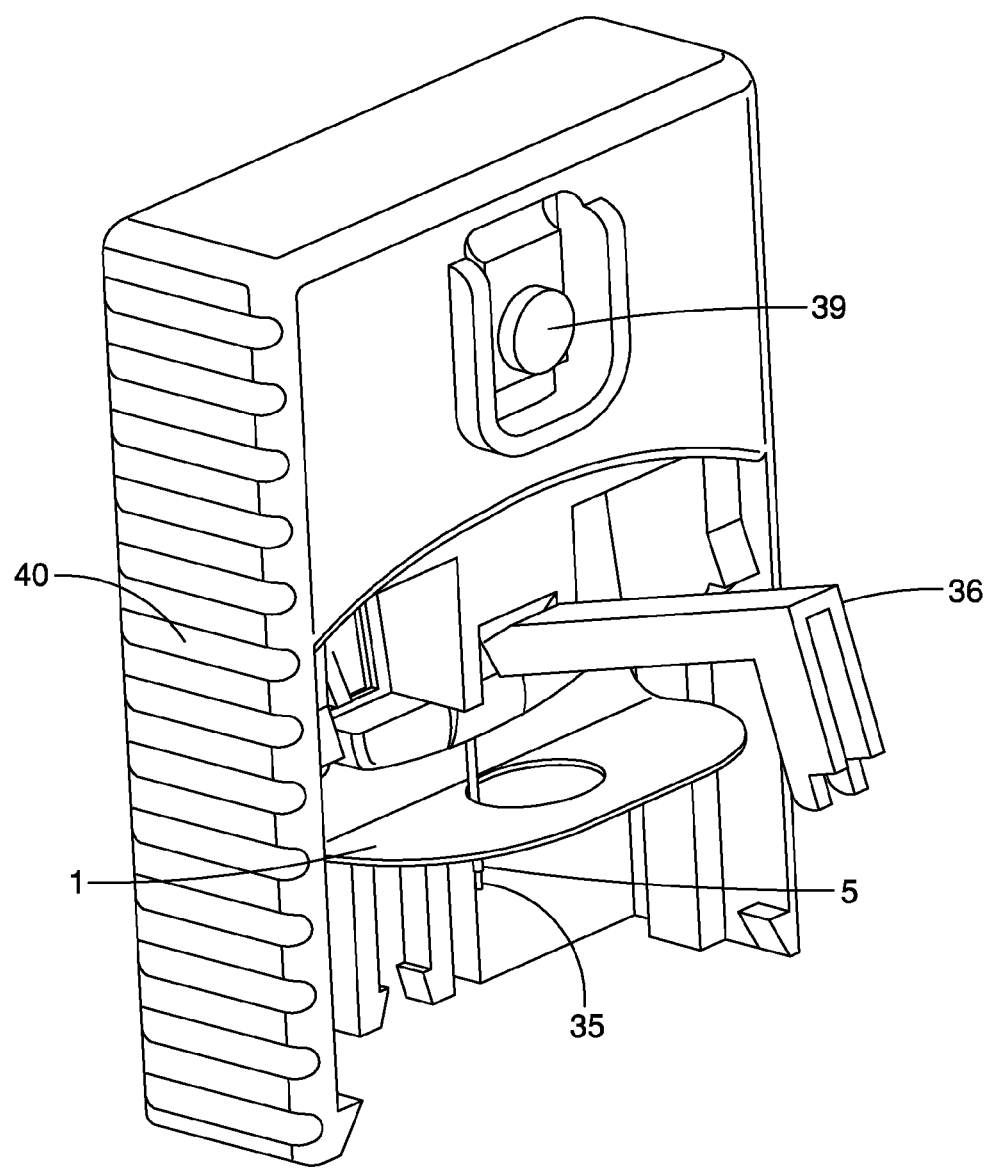
FIG. 13 shows the second embodiment of the injector device in a ready to use state.
Figure 14:
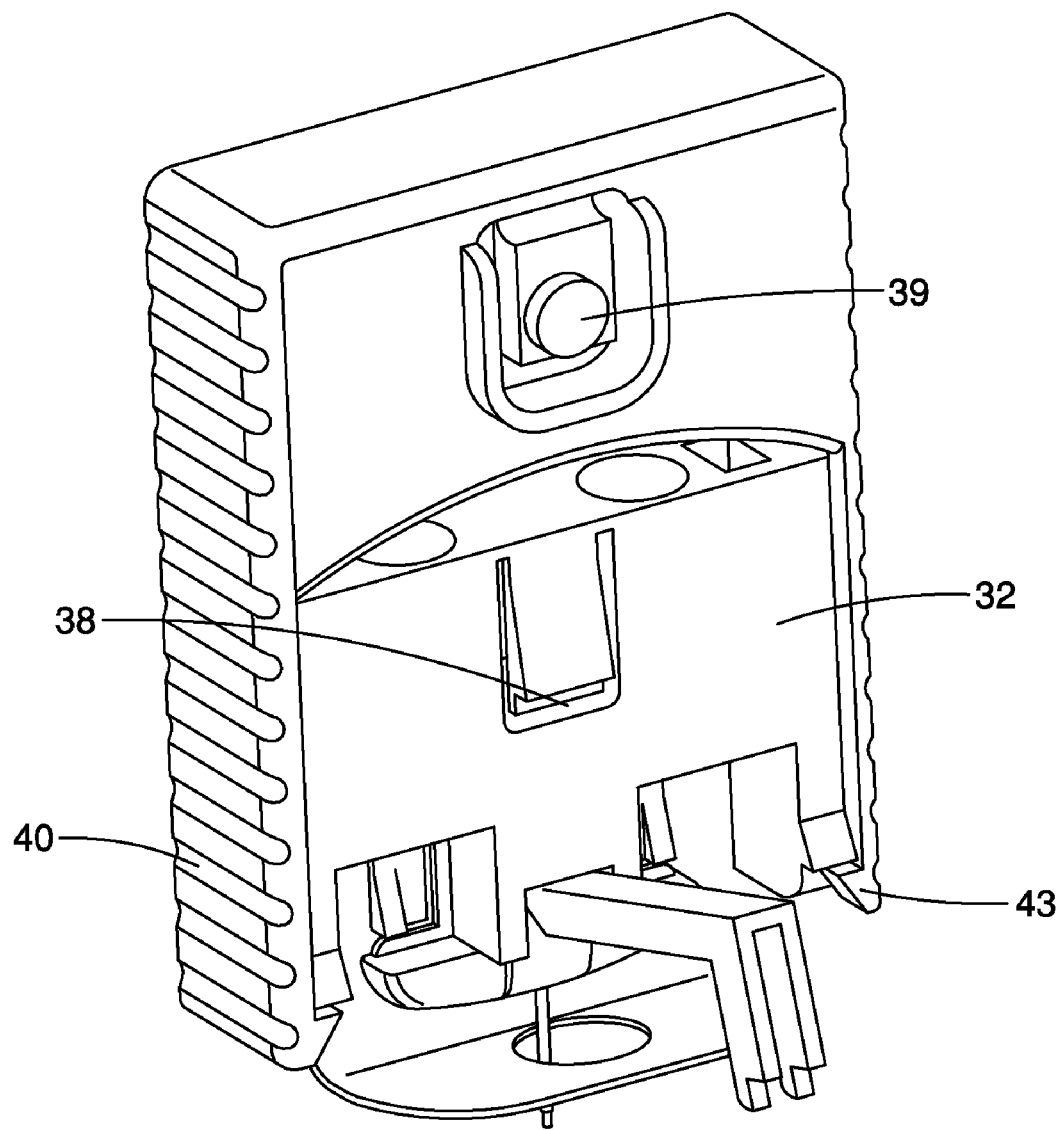
FIG. 14 shows the second embodiment of the injector device after insertion of the needle and before removing the injector from the infusion part.
Figure 16:
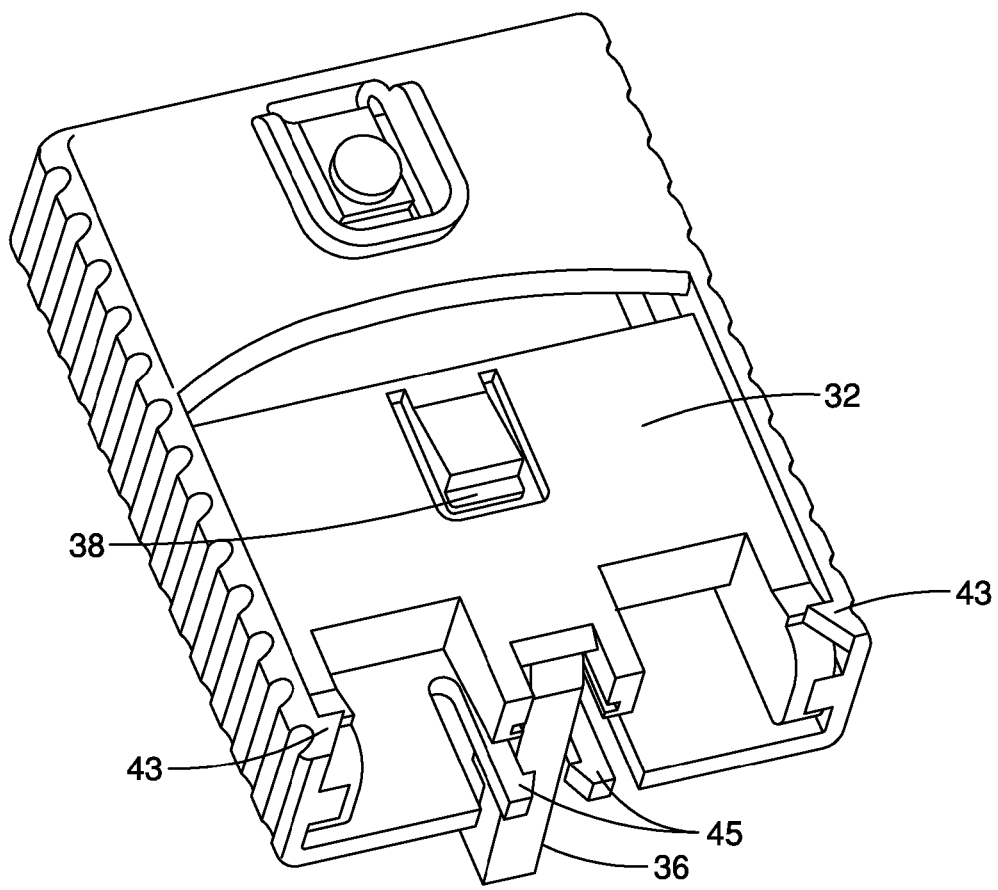
FIG. 16 shows the second embodiment of the injector device after the pivoting arm has been positioned to embrace the needle.
Figure 17:
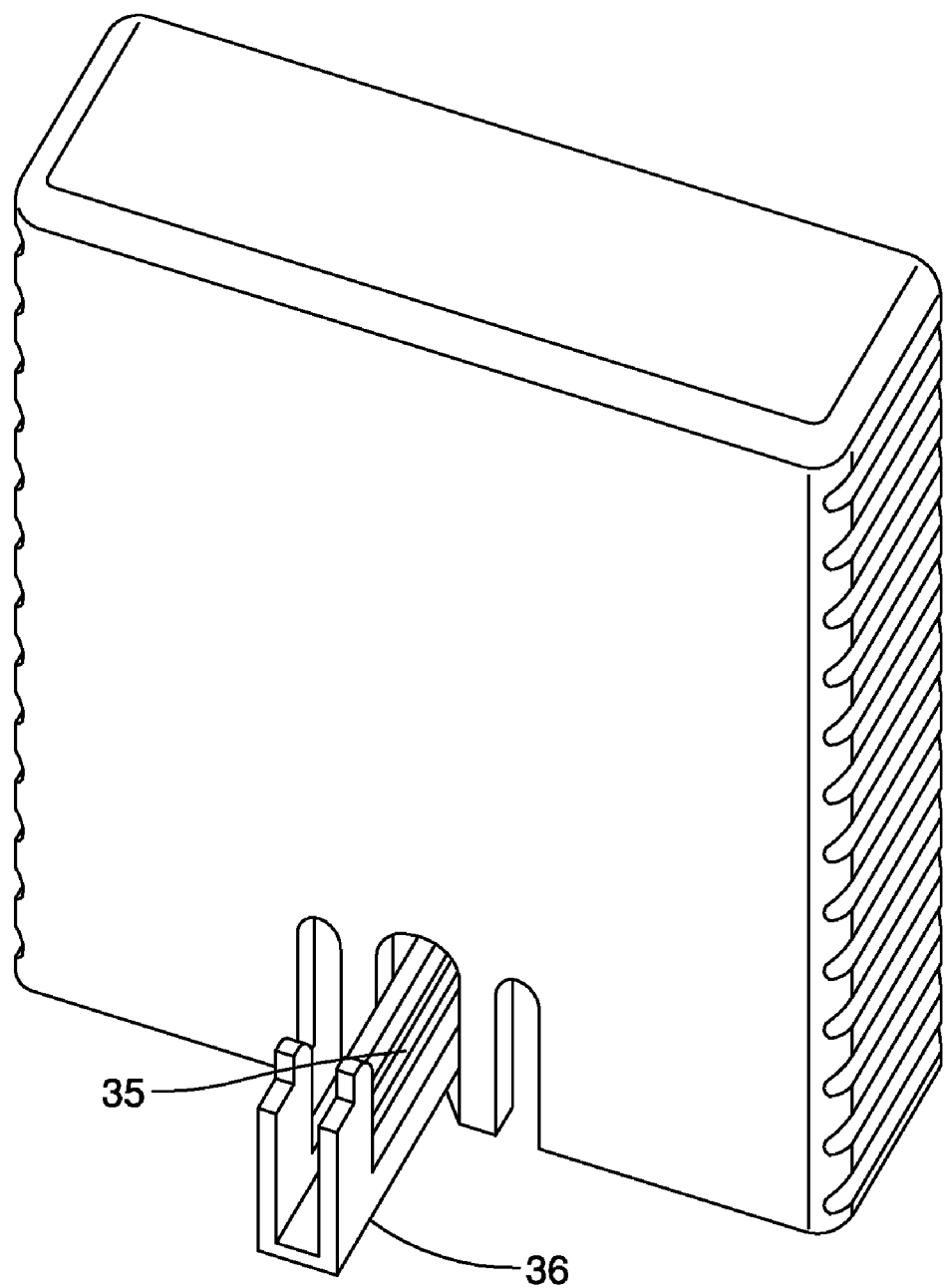
FIG. 17 shows the second embodiment of the injector device after the pivoting arm has been positioned to embrace the needle seen from another angle.
Figure 18:
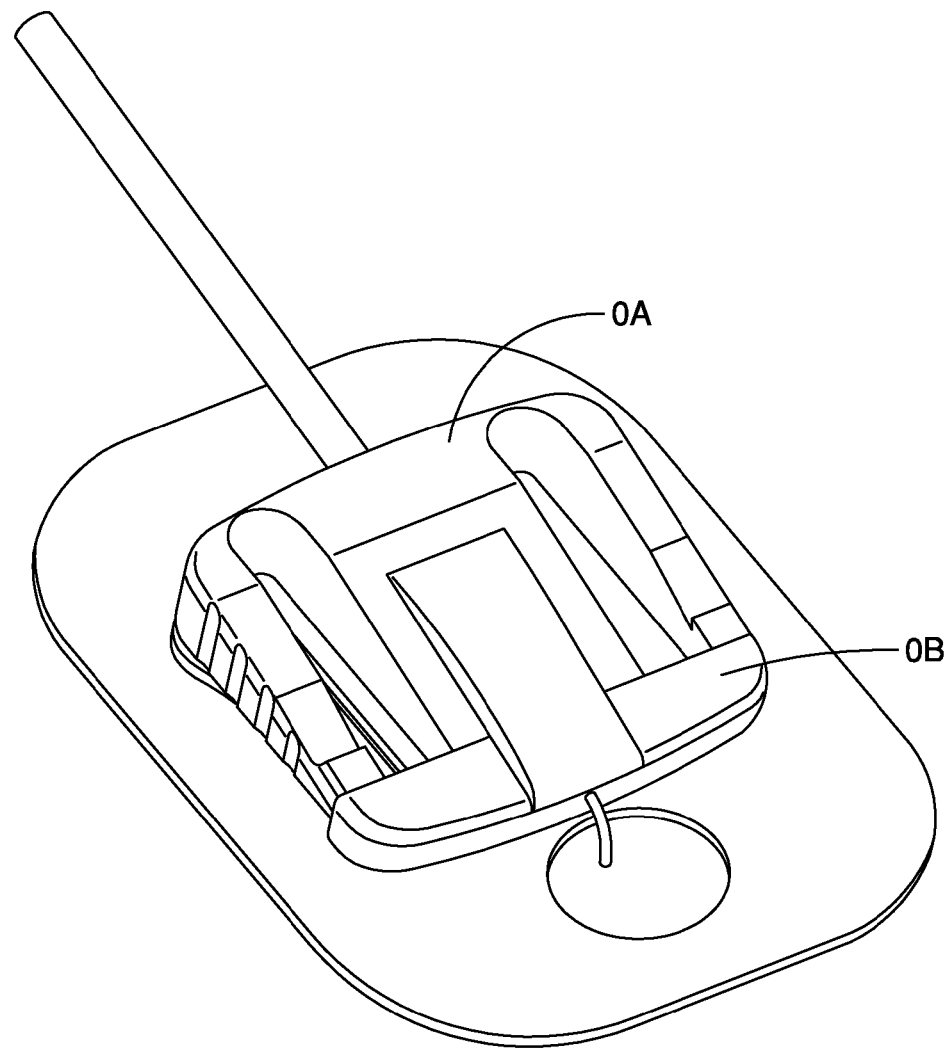
FIG. 18 shows an infusion set placed on the skin.

In FIG. 13 is shown an injector device prepared for insertion of the needle. The pivoting member is positioned away from the embracing position in an angle v<<90° in relation to the main axis of the injector device where the main axis is coincident with the insertion needle. The adhesive support (1) is positioned in such manner that the cannula (5) of the infusion part (0B) and the therein positioned needle (35) penetrates the adhesive support through an opening in the release liner. When the pivoting member is positioned essentially perpendicular to the main plane of the injector device it can provide a helping mean for achieving essentially vertical injection of the needle. Further FIG. 13 shows the needle (35) of the injector device inside the cannula (5). In FIG. 14 the injector device is in a released state where the needle (35) would have penetrated the skin. The housing in the embodiment of FIG. 14 has a stopping tab (43) corresponding to a protrusion on the slidable member that keeps the slidable member (32) within the housing (30) thereby making it easier to withdraw the needle since there is no risk that the slidable member slides out of the housing. In FIG. 15 the injector device has been withdrawn, leaving the cannula (5) of the infusion part (0B) inserted in the patient. In FIGS. 16 and 17 the pivoting member (36) is in a position where it embraces the needle (35) thereby protecting the surroundings from coming into contact with the used needle (35). In FIG. 18 the infusion part (OB) has been brought from the essentially vertical insertion position to a position essentially parallel to the skin.

Figure 19:
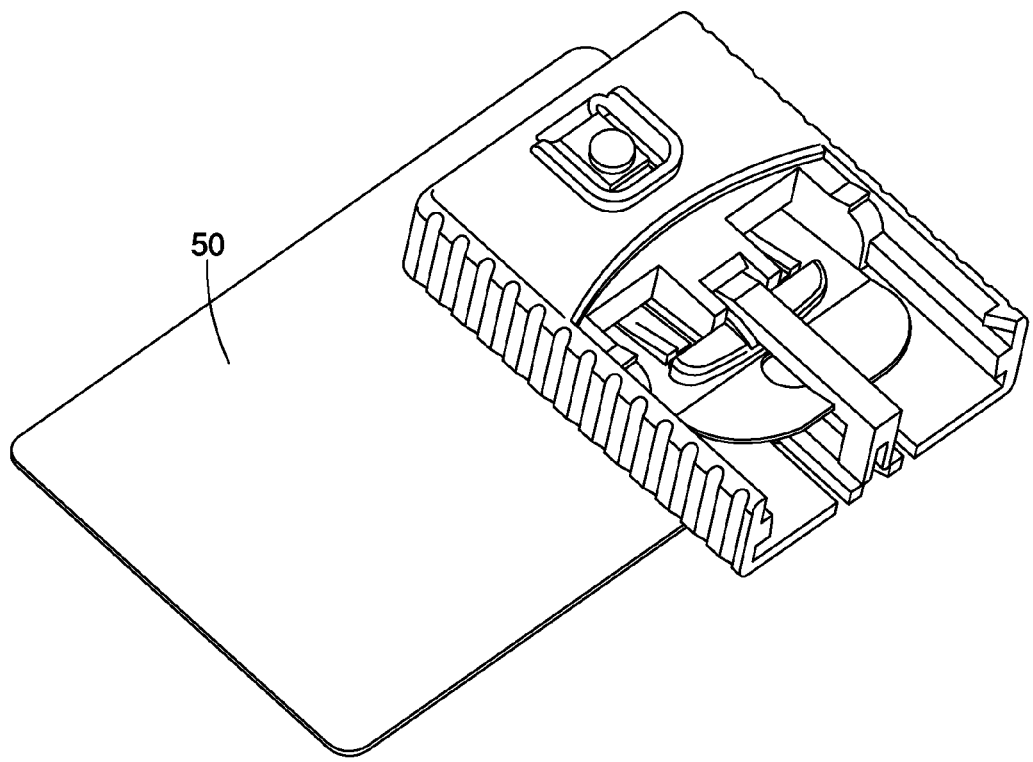
FIG. 19 shows the second embodiment of the injector device together with a credit card.

FIG. 19 shows the injector device together with a credit card to illustrate the size of the injector device.

Figure 20:
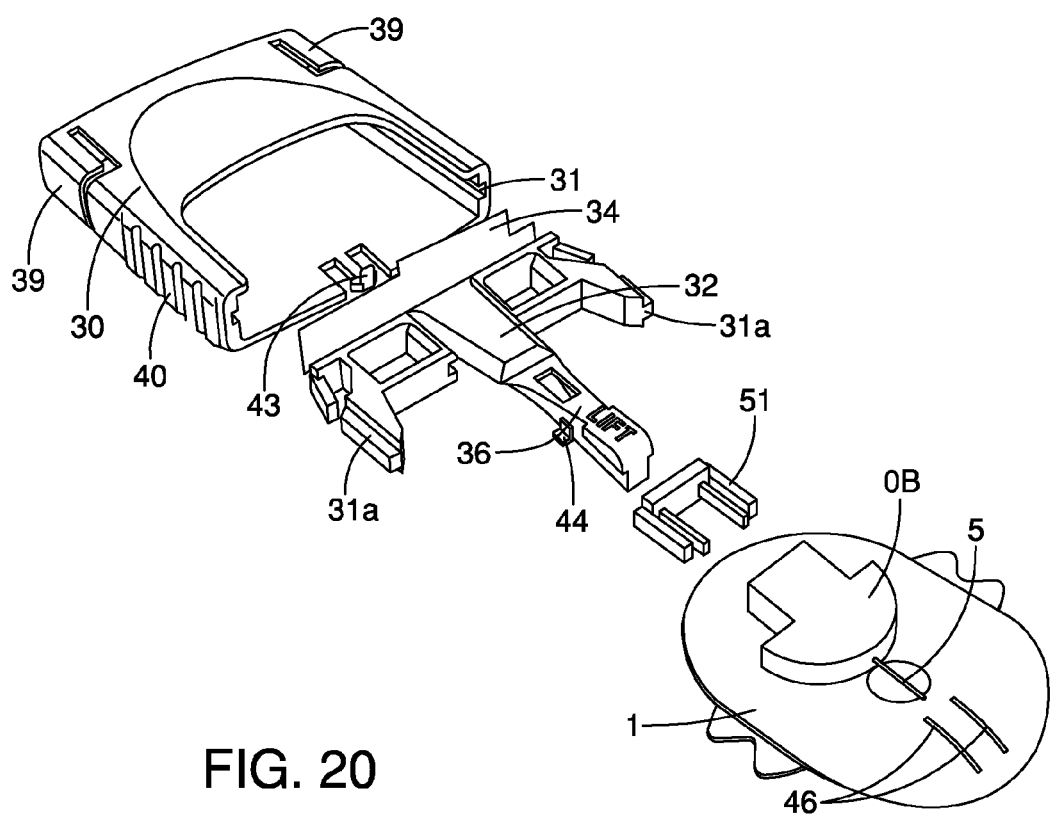
FIG. 20 shows a third embodiment of the injector device.

In FIG. 20 is shown a third embodiment of the injector device together with an infusion part (0B). This embodiment also has a housing (30) with longitudinally extending guiding means (31) and a longitudinally slidable member (32) of a different construction compared to the two first embodiments. Also the pivoting arm (36) and the spring (34) can be seen in this figure. In this embodiment the stopping tab (43) is placed centrally and has the form of a protrusion raising form the lower side of the housing (30). The release means (39) comprises two buttons placed on each side of the housing (30).

Figure 21:
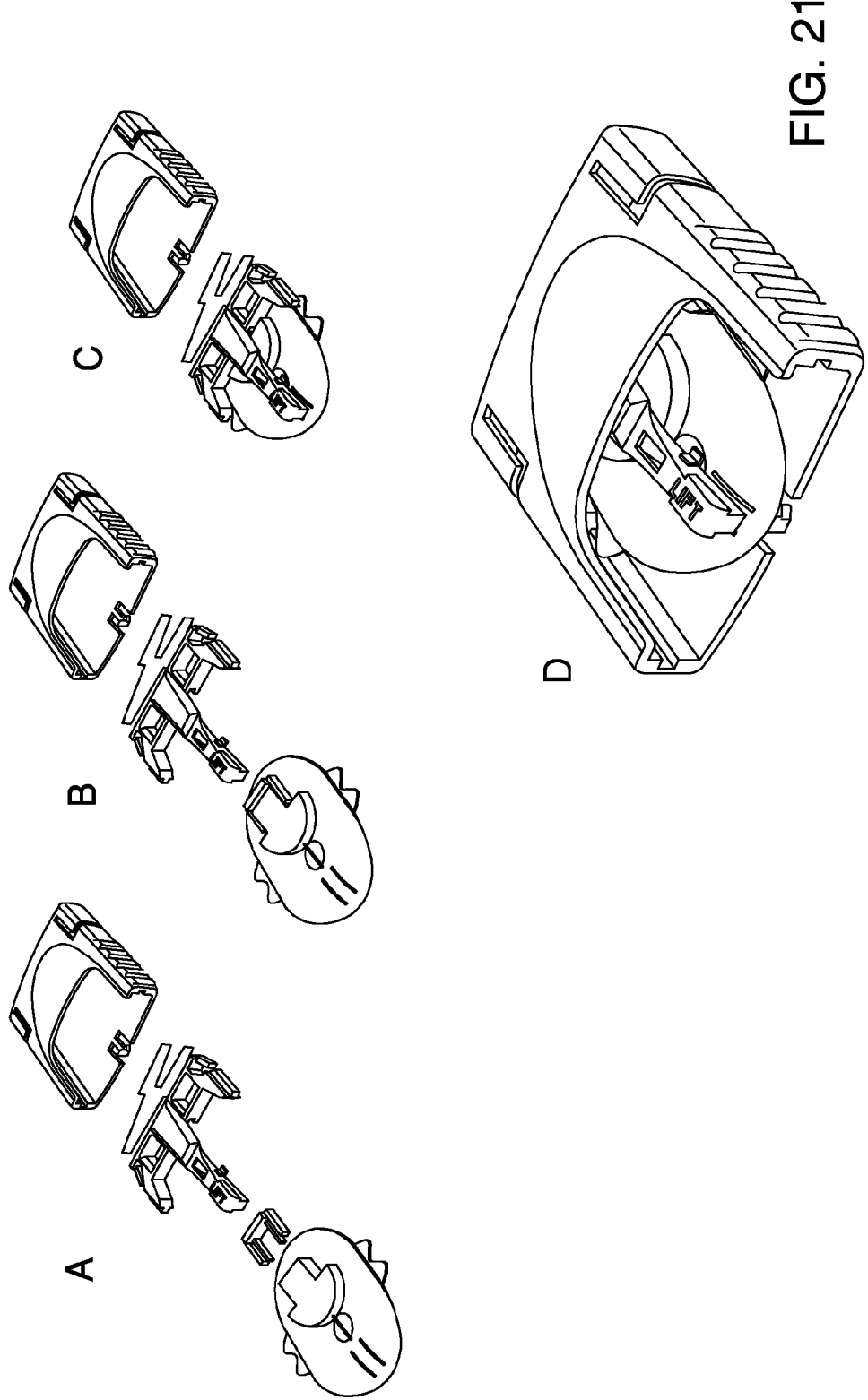

In FIG. 21 A-D it is shown how the infusion part (0B) along with the slidable member (32) and the spring (34) of the third embodiment fit into the housing (30). The unit (?) shown between the pivoting arm (36) and the insertion part (0B) is an adapter which makes it possible to use a standard injector for different guiding means (13) on the infusion part (0B).

In FIG. 22 A-B is shown fixing means (44) placed on the pivoting member (36). It is possible to temporarily attach a part of the adhesive support (1) to the fixing means in order to secure the position of the adhesive support in such a way that the adhesive surface of the support (1) will be turned towards the skin of the patient. Further release means (39) in the form of two buttons, one on each side of the housing (30), can be seen as well as the protruding stopping tab (43).

FIG. 23 A-B shows in further details and without the housing how the adhesive support (1) is hooked to the fixing means (44) due to at least one cutting (46) in the adhesive support (1).

FIG. 24 A shows the third embodiment of the injector device with an infusion part after insertion and 24 B shows the injector device after insertion and after the injector device has been removed from the insertion part (OB).

In FIG. 25 the pivoting member (36) of the injector device is in a position embracing the needle. A locking tab (45) fixes the pivoting arm in this position. This makes certain that the needle stays embraced by the pivoting arm and thereby minimizes the risk of somebody getting hurt by the needle.

FIG. 26 illustrates a third embodiment of an infusion part (0B). The infusion part (0B) comprises a base part (2) which base part (2) comprises a first set of guiding means (13) in the form of two stabilizing fins. The base part (2) comprises two retention devices (4) extending from the upper surface of the base part (2) and having a triangular form. The side of the triangular retention device facing the shoulder part (2a) is approximately perpendicular to the surface of the base part (2) and the side facing away from the shoulder part (2a) is sloping from the top of the retention device (4) to the surface of the base part (2). Mounted on the inner surface of the infusion part (0B) is the adhesive support (1). The cannula (5)

is extending from the shoulders (2a) of the base part (2) and is penetrating the adhesive support (1) being in fluid communication with the central cavity (3). The cavity (3) which can be covered by a membrane is adapted to receive a second cannula (6) extending from the connector. In this embodiment the base part (2) has two wide cuttings (12) creating two narrow flaps in the base part (2) on which the retention devices (4) are mounted.

The distance between (I) the side of the retention device (4) closest to the central part of the infusion part (OB) and (II) the central part of the infusion part (0B) defines how far it is possible to move the two arms (9) of the connector in the plane parallel to the base part (2). It is necessary for the corresponding means (10) in the arms (9) of the connector (0A) to be of less width than the distance between (I) and (II). In a preferred embodiment it would also be possible to free the connector (0A) from the infusion part (0B) by moving the arms (9) in a vertical direction away from the base part (2). If this should be possible the arms (9) of the connector need to be adequately flexible where the arms (9) are fixed to the central part of the connector. This can be done either by reducing the thickness of the arms (9) in at least on direction in this area until the desired flexibility is achieved or by choosing to construct the connector part (0A) of a material with a suitable flexibility.

In this embodiment the release liner (41, 42) of the adhesive support (1) is divided into to separated pieces. The first piece (41) is protecting the part of the adhesive support (1) in front of the cannula (5), and the second piece (42) is protecting the part of the adhesive support being behind the cannula (5) and under the infusion part. During insertion the two pieces are separated whereby the part of the adhesive in front of the cannula is bent up and the adhesive side of the adhesive support (1) is exposed around the cannula. The first piece (41) is either pulled back by the user or is attached to one side of the injector device; the second piece (42) is attached to the opposite side of the injector device.

FIGS. 35A-E and 36A-E illustrates the cycle of use of the injector device seen respectively from the upper (FIG. 35) and the lower (FIG. 36) side of the injector device.

In FIGS. 35A and 36A the device is in a first state, which is the state the device would normally be delivered to the patient in, under sterile conditions. In this state the pivoting arm (36) is in a position where it embraces the needle (35) and the angle v between the main plane of the injector device and the pivoting arm is approximately 0°, if the release means (39) should unintentionally be pressed in this situation two protruding tabs (48) will prevent the slidable member (32) from being pushed forward.

In FIGS. 35B and 36B the device is prepared for use by lifting the pivoting arm (36) backwards thereby exposing the insertion needle (35) and also in this embodiment lifting the part of the release liner (41) which is attached to the pivoting arm (36), exposing the underlying adhesive support (1). In this position the pivoting arm (36) allows for insertion of the needle and is in an angle v to main plane of the injector device where $90° \leq v \leq 180°$, and in this position the injector device would be placed against the patient's skin.

In FIGS. 35C and 36C the release means (39) has been pressed and has released the spring (34). The spring has pushed the slidable member (32) forward until the slidable member was stopped by two stopping tabs (43). In this position the insertion needle (35) has penetrated the patient's skin and a part (this part covers an area around the needle in the full breadth of the adhesive support) of the adhesive surface of the adhesive support (1) is in contact with the patient's skin. In FIG. 36C it is shown how the second part (42) of the release liner is attached to the housing (30) and still covers the adhesive surface when the slidable member (32) is pushed forward.

In FIGS. 35D and 36D it is shown what happens when the injector device is removed from the patient, leaving the infusion part (0B) inserted subcutaneously. The user frees the first part (41) of the release liner from the pivoting arm (36) and then when pulling the injector device away the second part (42) of the release liner is also pulled away, exposing the adhesive surface of the adhesive support (1) and making it possible for the user to press the adhesive support towards the skin and thereby securing the infusion part (0B).

Finally after withdrawal of the insertion needle which in this embodiment is attached to the slidable member (32) in the injector device, it is shown in FIGS. 35E and 36E how the pivoting member (36) is placed in a position where it is embracing the needle thereby protecting the surroundings from getting stung. In order to get into this position the pivoting arm (36) is turned approximately 180° from the position in FIGS. 35D and 36D, and the angle w between the main plane of the injector device and the pivoting arm (36) is approximately 90°.

The invention claimed is:

1. An infusion set comprising an infusion part for insertion into a patient and a connector for connecting the infusion part with a medical device through a tube, the connector being axially displaceable relative to the infusion part,
the infusion part comprising:
an adhesive support;
a base connected to the adhesive support, the base part including a first set of guides and at least two retention devices for releasably locking the connector to the infusion part, said retention devices extending upwardly from an upper surface of the base;
a first cannula extending from said base and being in fluid communication with a cavity, said cavity being adapted to receive a second cannula extending from the connector, wherein said second cannula is in fluid communication with the tube; and
the connector comprising:
a second set of guides adapted to fit with the first set of guides and at least two arms adapted to fit with the retention devices, the arms are movable in a laterally inward direction, in a laterally outward direction and in an upward direction away from the base such that movement of the arms in either the laterally inward direction, the laterally outward direction or the upward direction allows disengagement of the arms from the retention devices.

2. An infusion set according to claim 1, wherein the connector is symmetrical relative to a main plane of the connector and relative to a plane perpendicular to the main plane and parallel to the central axis.

3. An infusion set according to claim 1 wherein each arm is flexibly connected to the second set of guides in order for the arms to be able to move in the direction perpendicular to the base.

4. An infusion set according to claim 3, wherein the connection between each arm and the second set of guides comprises at least one groove.

5. An infusion set according to claim 1, wherein the retention devices are flexibly connected to the base.

6. An infusion set according to claim 5, wherein the base comprises at least two flaps on which the retention devices are positioned.

7. An infusion set according to claim 1, wherein the first cannula passes through the adhesive support.

8. An infusion set according to claim 1, wherein the adhesive support is a plaster.

9. An infusion set according to claim 1, wherein the infusion part and the connector comprise two different plastics materials.

10. An infusion set according to claim 1, wherein the visual tone of the connector and the base of the infusion part are different.

11. An infusion set according to claim 1, wherein each of the retention devices comprises a step.

12. An infusion set according to claim 1, wherein each of the retention devices comprises a triangular shape.

13. An infusion set according to claim 1, wherein the tube is fastened to the connector by glue.

14. An infusion set according to claim 1, wherein the medical device is an insulin pump.

15. An infusion set according to claim 1, wherein the first cannula comprises a thermoplastic elastomer (TPE).

16. An infusion set according to claim 15, wherein the thermoplastic elastomer is selected from the group consisting of polyester ethers, ECDEL, styrene based TPE, olefin based TPE, urethane based TPE, ester based TPE, amid based TPE, polyolefins and silicone rubbers.

17. An infusion set according to claim 1, wherein the infusion part the connector, or both comprise polypropylene.

18. An infusion set according to claim 1, wherein, the second cannula extends from a central part of the connector and the second cannula is recessed relative to a front portion of the central part and at least one of the first set of guides comprises at least two stabilizing fins.

19. An infusion set according to claim 1, further comprising an injector device for the subcutaneous introduction of the first cannula of the infusion part into the skin of a patient.

20. An infusion set according to claim 19, wherein the injector device comprises a housing, a back and longitudinally extending guide, a slidable member which is longitudinally slidable within the housing, a needle for insertion in the cavity of the first cannula, a spring located between the back of the housing and the longitudinally slidable member, locking members for maintaining the spring in a compressed state and release members for disengaging the locking members, and a pivoting member pivotable from a position allowing for insertion of the needle into a position wherein the pivoting member embraces the needle.

21. The infusion set according to claim 1, wherein said cavity is covered with a membrane.

22. The infusion set of claim 1 wherein the second cannula is received into the cavity in a horizontal direction parallel to a main plane of the base part.

23. An infusion set comprising an infusion part and a connector releasably connectable to the infusion part,
the infusion part comprising:
a base having a lower surface and an upper surface, the upper surface comprising a first guide and a releasable locking member extending upwardly from the upper surface for releasably connecting the infusion part to the connector; and
a first cannula extending outwardly from the base,
the connector comprising:
a second guide adapted to fit with the first guide;
an arm operably connected to the second guide for releasably interlocking with the locking member, the arm is movable in a laterally inward direction, in a laterally outward direction and in an upward direction away from the base such that movement of the arm in either the laterally inward direction, the laterally outward direction or the upward direction allows disengagement of the arm from the releasable locking member; and
a second cannula extending outwardly from the connector and adapted for reception at least partially within a cavity formed in the base;
wherein the first cannula and the second cannula are fluidly connectable.

24. The infusion set of claim 23, wherein the infusion set further comprises an adhesive layer connected to the lower surface of the base.

25. The infusion set of claim 23, comprising a membrane covering an opening of the cavity.

26. The infusion set of claim 23, wherein the base comprises a pair of first guides and a pair of locking members adapted to connect with a pair of second guides and a pair of arms on the connector.

27. The infusion set of claim 23, wherein the connector further comprises tubing fluidly connectable between the second cannula and a medication source.

* * * * *